(12) United States Patent
Gardner et al.

(10) Patent No.: US 9,506,073 B2
(45) Date of Patent: Nov. 29, 2016

(54) BLUE-LIGHT INDUCIBLE SYSTEM FOR GENE EXPRESSION

(71) Applicant: Board of Regents of the University of Texas System, Austin, TX (US)

(72) Inventors: Kevin H. Gardner, Dallas, TX (US); Laura B. Motta-Mena, Dallas, TX (US); Brian D. Zoltowski, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 96 days.

(21) Appl. No.: 14/359,030

(22) PCT Filed: Nov. 16, 2012

(86) PCT No.: PCT/US2012/065493
§ 371 (c)(1),
(2) Date: May 16, 2014

(87) PCT Pub. No.: WO2013/074911
PCT Pub. Date: May 23, 2013

(65) Prior Publication Data
US 2014/0325692 A1    Oct. 30, 2014

Related U.S. Application Data

(60) Provisional application No. 61/561,585, filed on Nov. 18, 2011.

(51) Int. Cl.
*C12N 15/63* (2006.01)
*C12N 9/02* (2006.01)

(52) U.S. Cl.
CPC ........... *C12N 15/635* (2013.01); *C12N 9/0069* (2013.01); *C12N 15/63* (2013.01); *C07K 2319/09* (2013.01); *C07K 2319/71* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 5,824,859 A | 10/1998 | Cashmore et al. | |
| 5,905,146 A | 5/1999 | Lecka-Czernik | |
| 5,959,081 A | 9/1999 | Lecka-Czernik | |
| 6,455,760 B1 | 9/2002 | Zhao et al. | |
| 6,723,557 B1 | 4/2004 | Sternberg et al. | |
| 6,733,996 B2 | 5/2004 | Froehlich et al. | |
| 6,849,717 B1 | 2/2005 | Sternberg et al. | |
| 7,645,569 B2 | 1/2010 | Gardner et al. | |
| 2004/0038400 A1* | 2/2004 | Froehlich ............... | C07H 21/04 435/446 |
| 2004/0121409 A1 | 6/2004 | Gardner et al. | |
| 2005/0074846 A1 | 4/2005 | Gardner et al. | |
| 2006/0051829 A1 | 3/2006 | Gardner et al. | |
| 2007/0050866 A1 | 3/2007 | Kiyosue et al. | |
| 2008/0148432 A1 | 6/2008 | Abad | |
| 2009/0054828 A1 | 2/2009 | Stolen et al. | |
| 2009/0054883 A1 | 2/2009 | Stolen et al. | |
| 2010/0221709 A1 | 9/2010 | Hockenbery et al. | |
| 2010/0304435 A1 | 12/2010 | Eggert et al. | |

FOREIGN PATENT DOCUMENTS

| | | |
|---|---|---|
| DE | 10 2005 048 828 | 4/2007 |
| JP | 2001-352851 | 12/2001 |
| JP | 2006-094704 | 4/2006 |
| JP | 2007-075019 | 3/2007 |
| JP | 2008-212063 | 9/2008 |
| JP | 2008-212064 | 9/2008 |
| JP | 2009-050175 | 3/2009 |
| WO | WO 92/19724 | 11/1992 |
| WO | WO 96/01897 | 1/1996 |
| WO | WO 02/40689 | 5/2002 |
| WO | WO 2004/058975 | 7/2004 |
| WO | WO 2005/033662 | 4/2005 |
| WO | WO 2007/120522 | 10/2007 |
| WO | WO 2009/025826 | 2/2009 |
| WO | WO 2011/002977 | 1/2011 |
| WO | WO 2011/035166 | 3/2011 |
| WO | WO 2011/041327 A1 | 4/2011 |
| WO | WO 2011/086840 A1 | 7/2011 |
| WO | WO 2011/116238 | 9/2011 |

OTHER PUBLICATIONS

Herrou et al. Function, structure and mechanism of bacterial photosensory LOV proteins. Nature Reviews Microbiology, vol. 9, pp. 713-723, Oct. 2011, published online Aug. 8, 2011.*
Blau et al., "Three functional classes of transcriptional activation domain," *Mol Cell Biol* 16(5):2044-2055, 1996.
Cheng, "Functional conservation of light, oxygen, or voltage domains in light sensing," *PNAS* 100(10):5938-5943, 2003.
Djouani-Tahri et al., "A eukaryotic LOV-histidine kinase with circadian clock function in the picoalga Ostreococcus," *The Plant Journal* 65:578-588, 2011.
Gardner et al., "A blue light inducible system for gene expression in eukaryotic cells: Adaptation of EL222 for biotechnological use," Sep. 13, 2011 presentation at UT Southwestern Medical Center.
GenBank Accession No. 3P7N_A, dated May 25, 2011.
International Search Report and Written Opinion for International Application No. PCT/US2012/065493, dated Apr. 24, 2013.

(Continued)

Primary Examiner — Jennifer Dunston
(74) Attorney, Agent, or Firm — Law Offices of Alan J. Morrison

(57) ABSTRACT

The present invention provides methods for light-dependent gene regulation using a light-responsive DNA-binding protein. Also provided are related nucleic acid molecules, and protein molecules, such as those encoding or comprising the light-responsive DNA-binding protein or DNA-binding sites recognizing the light-responsive DNA-binding protein. Kits using the present light-dependent gene regulation system are further provided by the present invention.

15 Claims, 15 Drawing Sheets

(56) References Cited

OTHER PUBLICATIONS

Kennedy et al., "Rapid blue light induction of protein interactions in living cells," *Nature Methods* 7(12):973-975, 2010.
Lamb et al., "Illuminating Solution Responses of a LOV Domain Protein with Photocoupled Small Angle X-Ray Scattering," *J Mol Biol* 393:909-919, 2009.
Moglich et al., "Engineered photoreceptors as novel optogenetic tools," *Photochem & Photobiol Sci* 9(10):1286, 2010.
Nash et al., "Structural basis of photosensitivity in a bacterial light-oxygen-voltage/helix-turn-helix (LOV-HTH) DNA-binding protein," *PNAS* 108(23):9449-9454, 2011.
Rivera-Cancel et al., "Identification of natural, and artificial DNA substrates for light-activated LOV-HTH transcription factor EL222," *Biochem* 51(50):10024-10034, 2012.
Shimizu-Sato et al., "A light-switchable gene promoter system," *Nature Biotechnology* 20:1041-1044, 2002.
Strickland et al., "Light-activated DNA binding in a designed allosteric protein," *PNAS* 105(31):10709-10714, 2008.
Takahashi et al., "Aureochrome, a photoreceptor required for photomorphogenesis in stramenopiles," *PNAS* 104:19625-19630, 2007.
Tuerk et al., "Systematic evolution of ligands by exponential enrichment: RNA ligands to bacteriophage T4 DNA polymerase," *Science* 249(4968):505-510, 1990.
Wu et al., "A genetically encoded photoactivatable Rac controls the motility of living cells," *Nature* 461:104-108, 2009.
Yazawa et al., "Induction of protein-protein interactions in live cells using light," *Nat Biotech* 27(10):941-945, 2009.
Zhu et al., "The quorum-sensing transcriptional regulator TraR requires its cognate signaling ligand for protein folding, protease resistance, and dimerization," *PNAS* 98(4):1507-1512, 2001.
Zoltowski et al., "Biophysical Studies of a LOV-HTH DNA Binding Protein," Gordon Research Seminar, Barga Italy, Apr. 17, 2010.
Zoltowski et al., "Light Activation of the LOV Protein Vivid Generates a Repidly Exchanging Dimer," *Biochem* 47:7012-7019, 2008.
Zoltowski et al., "Mechanism Based Tuning of a LOV Domain Photoreceptor," *Nat Chem Biol* 5:827-834, 2009.
Zoltowski et al., "Tripping the light fantastic: blue-light photoreceptors as examples of environmentally modulated protein-protein interactions," *Biochem* 50(1):4-16, 2011.
Zoltowski et al., "Variations in protein-flavin hydrogen bonding in a light, oxygen, voltage domain produce non-arrhenius kinetics of adduct decay," *Biochem* 50(41):8771-8779, 2011.

\* cited by examiner

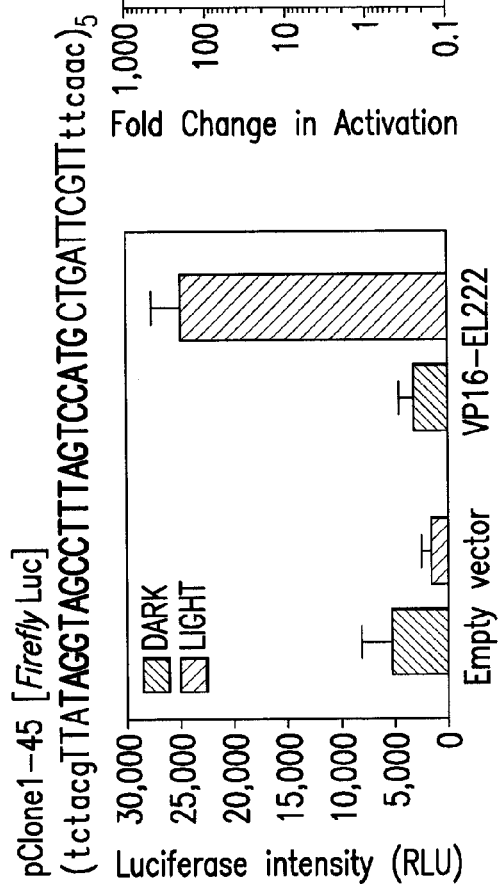
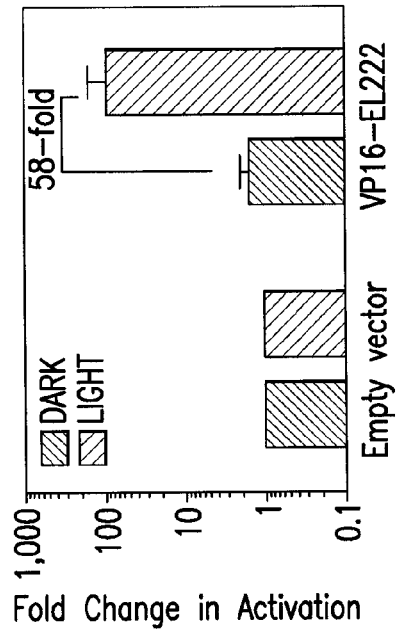
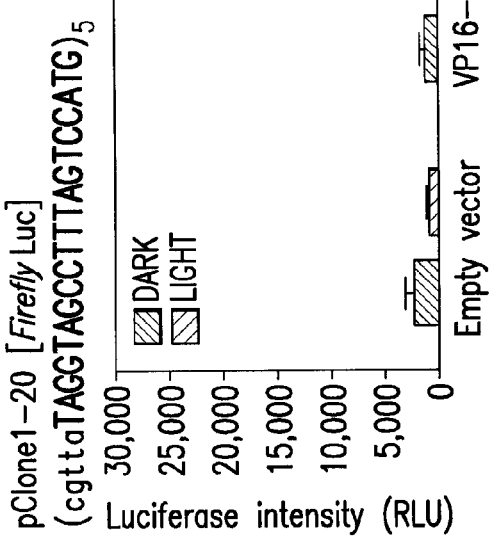
FIG.4A
FIG.4B

ATGGGC*CCTAAAAAGAAGCGTAAAGTC*GCCCCCCCGACCGATGTCAGCCTGGGGG

ACGAGCTCCACTTAGACGGCGAGGACGTGGCGATGGCGCATGCCGACGCGCTAGA

CGATTTCGATCTGGACATGTTGGGGGACGGGGATTCCCCGGGGCCGGGATTTACC

CCCCACGACTCCGCCCCCTACGGCGCTCTGGATATGGCCGACTTCGAGTTTGAGC

AGATGTTTACCGATGCCCTTGGAATTGACGAGTACGGTGGGGAATTCGGGGCAGA

CGACACACGCGTTGAGGTGCAACCGCCGGCGCAGTGGGTCCTCGACCTGATCGAG

GCCAGCCCGATCGCATCGGTCGTGTCCGATCCGCGTCTCGCCGACAATCCGCTGA

TCGCCATCAACCAGGCCTTCACCGACCTGACCGGCTATTCCGAAGAAGAATGCGT

CGGCCGCAATTGCCGATTCCTGGCAGGTTCCGGCACCGAGCCGTGGCTGACCGAC

AAGATCCGCCAAGGCGTGCGCGAGCACAAGCCGGTGCTGGTCGAGATCCTGAACT

ACAAGAAGGACGGCACGCCGTTCCGCAATGCCGTGCTCGTTGCACCGATCTACGA

TGACGACGACGAGCTTCTCTATTTCCTCGGCAGCCAGGTCGAAGTCGACGACGAC

CAGCCCAACATGGGCATGGCGCGCCGCGAACGCGCCGCGGAAATGCTCAGGACGC

TGTCGCCGCGCCAGCTCGAGGTTACGACGCTGGTGGCATCGGGCTTGCGCAACAA

GGAAGTGGCGGCCCGGCTCGGCCTGTCGGAGAAAACCGTCAAGATGCACCGCGGG

CTGGTGATGGAAAAGCTCAACCTGAAGACCAGCGCCGATCTGGTGCGCATTGCCG

TCGAAGCCGGAATCTAA

FIG.6

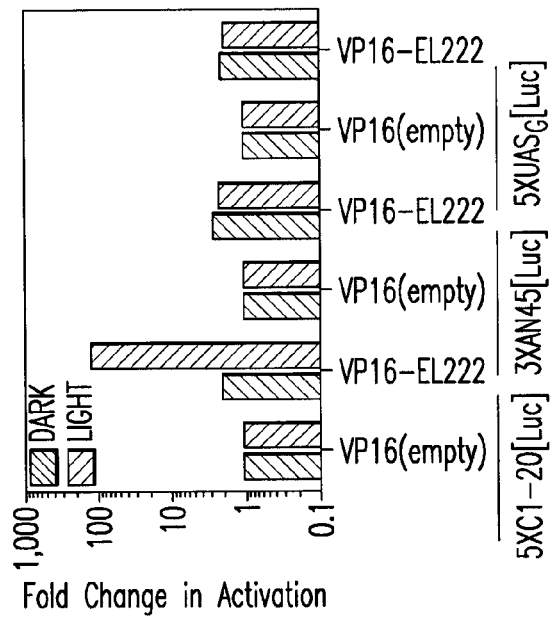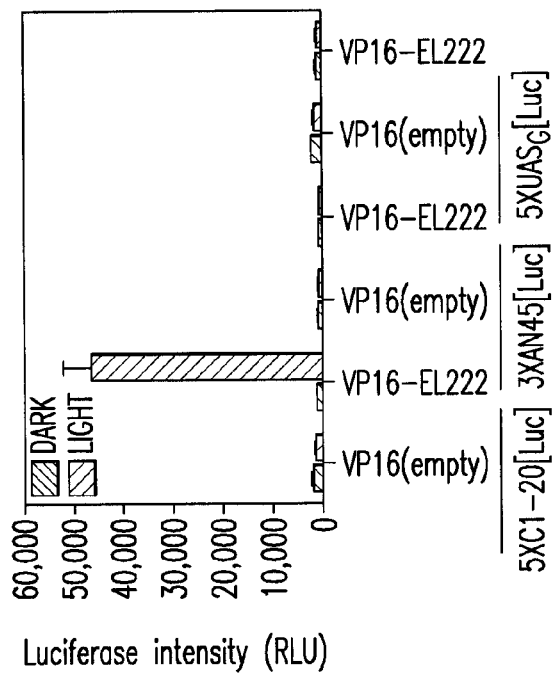
FIG. 7A
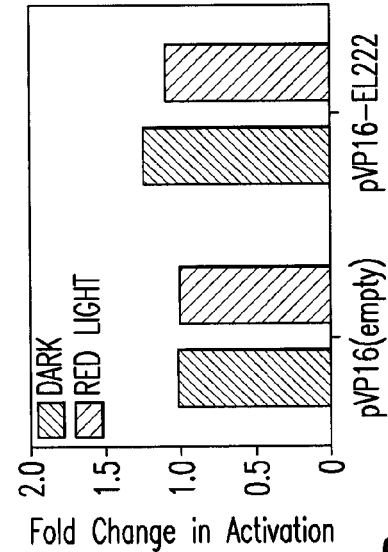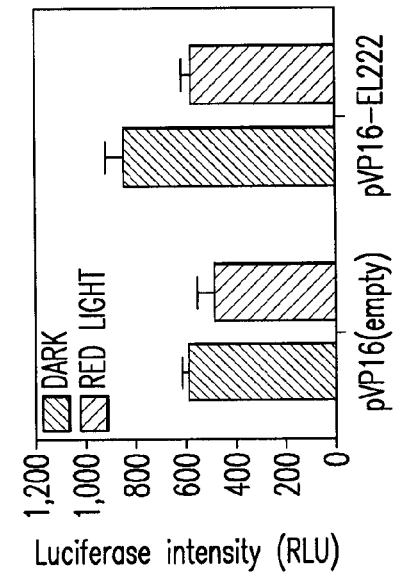
FIG. 7B

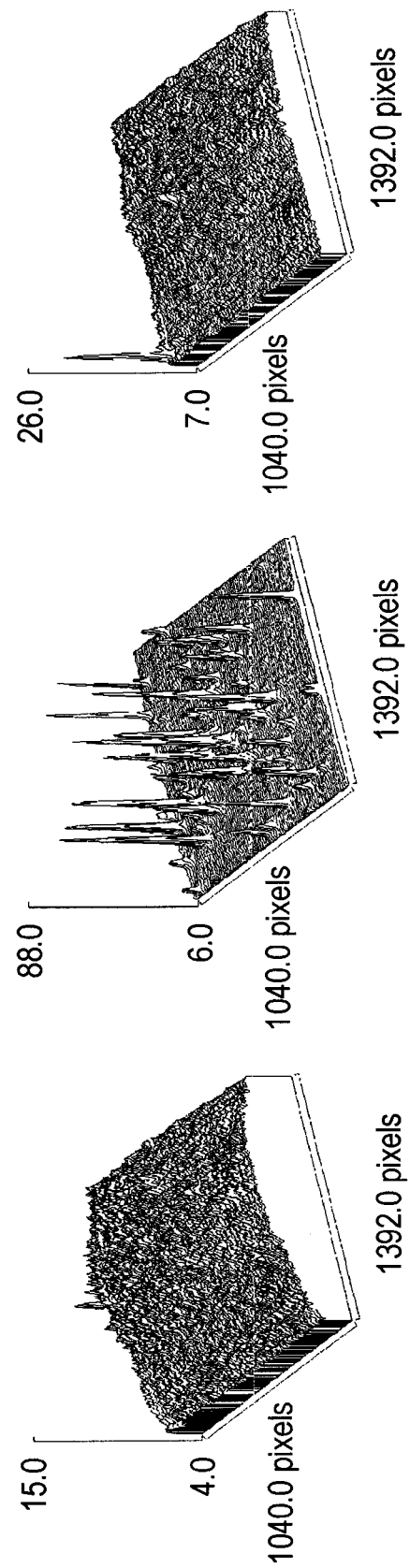

SEQUENCE LISTING

<160> NUMBER OF SEQ ID NOS: 85

<210> SEQ ID NO 1
<211> LENGTH: 75
<212> TYPE: DNA
<213> ORGANISM: Artificial sequence
<220> FEATURE:
<223> OTHER INFORMATION: Single-stranded oligonucleotide
<220> FEATURE:
<221> NAME/KEY: misc_feature
<222> LOCATION: (22)..(54)
<223> OTHER INFORMATION: n is a, c, g, or t

<400> SEQUENCE: 1
gggaatggat ccacatctac gnnnnnnnnn nnnnnnnnnn nnnnnnnnnn nnnnttcaac    60
ttgacgaagc ttgcc                                                    75

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
gggaatggat ccacatctac g                                             21

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
ggcaagcttc gtcaagttga a                                             21

<210> SEQ ID NO 4
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 4
ttataggtag cctttagtcc atgctgattc gtt                                33

<210> SEQ ID NO 5
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 5
tagacttaag tctagtacac aagtttttcca ggg                               33

<210> SEQ ID NO 6
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 6
agctaggctt ttggtctgta tagctgtctt ata                                33

```
<210> SEQ ID NO 7
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 7
tatagggctt tagtctgtat gtgggatgtg tgt                                    33

<210> SEQ ID NO 8
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 8
catggcctaa ggactgtaag tactattaaa tac                                    33

<210> SEQ ID NO 9
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 9
cagatacatg ctttagtacg tatattcgat gtc                                    33

<210> SEQ ID NO 10
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 10
gccctaagac tgtatcttat tcgtgagttt taa                                    33

<210> SEQ ID NO 11
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 11
aaatcgaggg gccgaggtct cctttccttg aca                                    33

<210> SEQ ID NO 12
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 12
accttacaaa gctaataatt cttccttcaa acg                                    33

<210> SEQ ID NO 13
<211> LENGTH: 33
<212> TYPE: DNA
<213> ORGANISM: Artificial sequence
<220> FEATURE:
```

<223> OTHER INFORMATION: Single-stranded oligonucleotide

<400> SEQUENCE: 13
tgttcagggg tatgcctacg ctggatcagc cgt                33

<210> SEQ ID NO 14
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 14
gtgaccgttc cgtattcatt attcacacat aat                33

<210> SEQ ID NO 15
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 15
tcgcattaga atggctggga cggttagtgt tgg                33

<210> SEQ ID NO 16
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 16
ttaggcactt gtgacttgac gttgtttgta cat                33

<210> SEQ ID NO 17
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 17
ttctgaggaa gatgaagatg acaggcatgt gta                33

<210> SEQ ID NO 18
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 18
cagtctttct ctctcgtcga cgatgtattt tct                33

<210> SEQ ID NO 19
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 19 attttggtg ggagtattag tacgaacggc tgt                 33

```
<210> SEQ ID NO 20
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 20
ttcaatcgct agctacctta ctcgttaata aag                            33

<210> SEQ ID NO 21
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 21
gaccaaagtg caatggtcca attcggttat gcc                            33

<210> SEQ ID NO 22
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 22
gtatttaatt gcagagaaaa tctttatctt ctt                            33

<210> SEQ ID NO 23
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 23
gttcgctttg aatgtaacgg actcgtgaga ttt                            33

<210> SEQ ID NO 24
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 24
cattcaaaag tacgcgaggt tttggtgcta ctt                            33

<210> SEQ ID NO 25
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 25
gtctaaggac taggtgtgtt cctctggatc tcg                            33

<210> SEQ ID NO 26
<211> LENGTH: 33
<212> TYPE: DNA
<213> ORGANISM: Artificial sequence
<220> FEATURE:
<223> OTHER INFORMATION: Single-stranded oligonucleotide
```

<400> SEQUENCE: 26
agggtcgctc agcataaagg ttgcaattac ggt                                    33

<210> SEQ ID NO 27
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 27
aaagtctagt attgtacacc tcctctcggt aaa                                    33

<210> SEQ ID NO 28
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 28
atcagggaca tagaacgcta agactcgcct gca                                    33

<210> SEQ ID NO 29
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 29
ggtgccggtg agtaccatgg accttggtaa ctt                                    33

<210> SEQ ID NO 30
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 30
aagtgacgat tacataccc gtataccgta tca                                     33

<210> SEQ ID NO 31
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 31
ctgatactat agctaccttt gatggttttc ata                                    33

<210> SEQ ID NO 32
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 32
gtcttttggg catgttgtga ataagaagcc aaa                                    33

<210> SEQ ID NO 33
<211> LENGTH: 33

```
<212> TYPE: DNA
<213> ORGANISM: Artificial sequence
<220> FEATURE:
<223> OTHER INFORMATION: Single-stranded oligonucleotide

<400> SEQUENCE: 33
acaaaagcct gtgcggtaag aaatgagttt taa                                   33

<210> SEQ ID NO 34
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 34
acccagtcga cttcaaggat ataataaacc cgt                                   33

<210> SEQ ID NO 35
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 35
tacttaagga ctatataagg gtttactgat cgt                                   33

<210> SEQ ID NO 36
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 36
ttggtacatt atacaagcgt gagaggactg gct                                   33

<210> SEQ ID NO 37
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 37
tcgaaaagct acggtcatta tgtaggactg tcg                                   33

<210> SEQ ID NO 38
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 38
tacgttgggt gttttttaat cccggaaatg cgt                                   33

<210> SEQ ID NO 39
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 39
```
cagtctttat ctctcgtcga cgatgtattt tct                33

<210> SEQ ID NO 40
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 40
cgtcgatgag aacctcggag acatggccag tct                33

<210> SEQ ID NO 41
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 41
ctatgtatct acgtgaatgg atacggtctt ttt                33

<210> SEQ ID NO 42
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 42
tattaagcct aggggtccta ttacccttag act                33

<210> SEQ ID NO 43
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 43
ctataggtga ctgcgggtat gagagtagtg gga                33

<210> SEQ ID NO 44
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 44
tagcccattt attgtttgaa agcgcatttg tca                33

<210> SEQ ID NO 45
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 45
gttatgtttg gcgacgcgcc ggttagtctc ctt                33

<210> SEQ ID NO 46
<211> LENGTH: 33
<212> TYPE: DNA
<213> ORGANISM: Artificial sequence

```
<220> FEATURE:
<223> OTHER INFORMATION: Single-stranded oligonucleotide

<400> SEQUENCE: 46
gcctttatgc ttatacgtgc cgatttccca aat                                  33

<210> SEQ ID NO 47
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 47
ttattaagtc cgtattaagt atggagggag agg                                  33

<210> SEQ ID NO 48
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 48
gcacaatgtc caccctcacg ccatacttat tga                                  33

<210> SEQ ID NO 49
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 49
gttccttggg atgagctcgt atgcacatgg tat                                  33

<210> SEQ ID NO 50
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 50
ggttgaatag ttataatgcg acctggactc ttt                                  33

<210> SEQ ID NO 51
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 51
caaacgtcat ggtcaacgta tttacactag atc                                  33

<210> SEQ ID NO 52
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 52
tgttgagttc ataggaaggg gctgtagaca ttc                                  33
```

<210> SEQ ID NO 53
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 53
ccatttgaga tgtatagcgg accagaaatg gtt                                    33

<210> SEQ ID NO 54
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 54
cgattgactg tatggacctt aatatagttt gta                                    33

<210> SEQ ID NO 55
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 55
tactatagga ttgttagccc tgaagagcag gtg                                    33

<210> SEQ ID NO 56
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 56
cagtgcgcta gctaatactc ccttgtttta cct                                    33

<210> SEQ ID NO 57
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 57
accttatgac caggttgttg gactgattgt aac                                    33

<210> SEQ ID NO 58
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 58
tccttcagtc tctacttatt aaaggcttga aag                                    33

<210> SEQ ID NO 59
<211> LENGTH: 33
<212> TYPE: DNA
<213> ORGANISM: Artificial sequence
<220> FEATURE:
<223> OTHER INFORMATION: Single-stranded oligonucleotide

```
<400> SEQUENCE: 59
tcaggggaca ttgggctacg attatctacc tta                           33

<210> SEQ ID NO 60
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 60
gtcgttagga ggtactttga acgccaccat cat                           33

<210> SEQ ID NO 61
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 61
cctgcttggc aagatcttac cggggtttgg tag                           33

<210> SEQ ID NO 62
<211> LENGTH: 33
<212> TYPE: DNA
<213> ORGANISM: Artificial sequence
<220> FEATURE:
<223> OTHER INFORMATION: Single-stranded oligonucleotide

<400> SEQUENCE: 62
gtatttaagc catactattg tcttagccgc gag                           33

<210> SEQ ID NO 63
<211> LENGTH: 20
<212> TYPE: DNA
<213> ORGANISM: Artificial sequence
<220> FEATURE:
<223> OTHER INFORMATION: Single-stranded oligonucleotide

<400> SEQUENCE: 63
tctacgttat aggtagcctt                                          20

<210> SEQ ID NO 64
<211> LENGTH: 20
<212> TYPE: DNA
<213> ORGANISM: Artificial sequence
<220> FEATURE:
<223> OTHER INFORMATION: Single-stranded oligonucleotide

<400> SEQUENCE: 64
taggtagcct ttagtccatg                                          20

<210> SEQ ID NO 65
<211> LENGTH: 20
<212> TYPE: DNA
<213> ORGANISM: Artificial sequence
<220> FEATURE:
<223> OTHER INFORMATION: Single-stranded oligonucleotide

<400> SEQUENCE: 65
tttagtccat gctgattcgt                                          20

<210> SEQ ID NO 66
```

```
<211> LENGTH: 20
<212> TYPE: DNA
<213> ORGANISM: Artificial sequence
<220> FEATURE:
<223> OTHER INFORMATION: Single-stranded oligonucleotide

<400> SEQUENCE: 66
tgctgattcg ttttcaactt                                              20

<210> SEQ ID NO 67
<211> LENGTH: 14
<212> TYPE: DNA
<213> ORGANISM: Artificial sequence
<220> FEATURE:
<223> OTHER INFORMATION: Single-stranded oligonucleotide
<220> FEATURE:
<221> NAME/KEY: misc_feature
<222> LOCATION: (2)..(2)
<223> OTHER INFORMATION: s is c or g
<220> FEATURE:
<221> NAME/KEY: misc_feature
<222> LOCATION: (6)..(6)
<223> OTHER INFORMATION: w is a or t
<220> FEATURE:
<221> NAME/KEY: misc_feature
<222> LOCATION: (7)..(7)
<223> OTHER INFORMATION: r is g or a
<220> FEATURE:
<221> NAME/KEY: misc_feature
<222> LOCATION: (9)..(9)
<223> OTHER INFORMATION: w is a or t
<220> FEATURE:
<221> NAME/KEY: misc_feature
<222> LOCATION: (11)..(11)
<223> OTHER INFORMATION: y is t or c

<400> SEQUENCE: 67
gscttwrgwc ygta                                                    14

<210> SEQ ID NO 68
<211> LENGTH: 45
<212> TYPE: DNA
<213> ORGANISM: Artificial sequence
<220> FEATURE:
<223> OTHER INFORMATION: Single-stranded oligonucleotide

<400> SEQUENCE: 68
tctacgttat aggtagcctt tagtccatgc tgattcgttt tcaac                  45

<210> SEQ ID NO 69
<211> LENGTH: 25
<212> TYPE: DNA
<213> ORGANISM: Artificial sequence
<220> FEATURE:
<223> OTHER INFORMATION: Single-stranded oligonucleotide

<400> SEQUENCE: 69
cgttataggt agcctttagt ccatg                                        25

<210> SEQ ID NO 70
<211> LENGTH: 897
<212> TYPE: DNA
<213> ORGANISM: Artificial sequence
<220> FEATURE:
<223> OTHER INFORMATION: NLS-VP16-EL222 (14-222aa) nucleotide sequence

<400> SEQUENCE: 70
atgggcccta aaagaagcg taaagtcgcc ccccgaccg atgtcagcct gggggacgag    60
ctccacttag acggcgagga cgtggcgatg gcgcatgccg acgcgctaga cgatttcgat   120
```

```
ctggacatgt tgggggacgg ggattccccg gggccgggat ttaccccca cgactccgcc      180 ccctacggcg ctctggatat ggccgacttc gagtttgagc agatgtttac cgatgccctt      240
ggaattgacg agtacggtgg ggaattcggg gcagacgaca cacgcgttga ggtgcaaccg      300
ccggcgcagt gggtcctcga cctgatcgag gccagcccga tcgcatcggt cgtgtccgat      360
ccgcgtctcg ccgacaatcc gctgatcgcc atcaaccagg ccttcaccga cctgaccggc      420
tattccgaag aagaatgcgt cggccgcaat tgccgattcc tggcaggttc cggcaccgag      480
ccgtggctga ccgacaagat ccgccaaggc gtgcgcgagc acaagccggt gctggtcgag      540
atcctgaact acaagaagga cggcacgccg ttccgcaatg ccgtgctcgt tgcaccgatc      600
tacgatgacg acgacgagct tctctatttc ctcggcagcc aggtcgaagt cgacgacgac      660
cagcccaaca tgggcatggc gcgccgcgaa cgcgccgcgg aaatgctcag gacgctgtcg      720
ccgcgccagc tcgaggttac gacgctggtg gcatcgggct tgcgcaacaa ggaagtggcg      780
gcccggctcg gcctgtcgga gaaaaccgtc aagatgcacc gcgggctggt gatggaaaag      840
ctcaacctga agaccagcgc cgatctggtg cgcattgccg tcgaagccgg aatctaa       897
```

<210> SEQ ID NO 71
<211> LENGTH: 298
<212> TYPE: PRT
<213> ORGANISM: Artificial sequence
<220> FEATURE:
<223> OTHER INFORMATION: NLS-VP16-EL222 protein sequence

<400> SEQUENCE: 71

```
Met Gly Pro Lys Lys Arg Lys Val Ala Pro Thr Asp Val Ser
1               5                   10                  15

Leu Gly Asp Glu Leu His Leu Asp Gly Glu Asp Val Ala Met Ala His
                20                  25                  30

Ala Asp Ala Leu Asp Asp Phe Asp Leu Asp Met Leu Gly Asp Gly Asp
            35                  40                  45

Ser Pro Gly Pro Gly Phe Thr Pro His Asp Ser Ala Pro Tyr Gly Ala
        50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Gly Ala Asp Asp Thr Arg Val
                85                  90                  95

Glu Val Gln Pro Pro Ala Gln Trp Val Leu Asp Leu Ile Glu Ala Ser
            100                 105                 110

Pro Ile Ala Ser Val Val Ser Asp Pro Arg Leu Ala Asp Asn Pro Leu
        115                 120                 125

Ile Ala Ile Asn Gln Ala Phe Thr Asp Leu Thr Gly Tyr Ser Glu Glu
    130                 135                 140

Glu Cys Val Gly Arg Asn Cys Arg Phe Leu Ala Gly Ser Gly Thr Glu
145                 150                 155                 160

Pro Trp Leu Thr Asp Lys Ile Arg Gln Gly Val Arg Glu His Lys Pro
                165                 170                 175

Val Leu Val Glu Ile Leu Asn Tyr Lys Lys Asp Gly Thr Pro Phe Arg
            180                 185                 190

Asn Ala Val Leu Val Ala Pro Ile Tyr Asp Asp Asp Glu Leu Leu
        195                 200                 205

Tyr Phe Leu Gly Ser Gln Val Glu Val Asp Asp Gln Pro Asn Met
    210                 215                 220
```

```
Gly Met Ala Arg Arg Glu Arg Ala Ala Glu Met Leu Arg Thr Leu Ser
225                 230                 235                 240

Pro Arg Gln Leu Glu Val Thr Thr Leu Val Ala Ser Gly Leu Arg Asn
            245                 250                 255

Lys Glu Val Ala Ala Arg Leu Gly Leu Ser Glu Lys Thr Val Lys Met
        260                 265                 270

His Arg Gly Leu Val Met Glu Lys Leu Asn Leu Lys Thr Ser Ala Asp
    275                 280                 285

Leu Val Arg Ile Ala Val Glu Ala Gly Ile
    290                 295

<210> SEQ ID NO 72
<211> LENGTH: 630
<212> TYPE: DNA
<213> ORGANISM: Erythrobacter litoralis

<400> SEQUENCE: 72
ggggcagacg acacacgcgt tgaggtgcaa ccgccggcgc agtgggtcct cgacctgatc      60
gaggccagcc cgatcgcatc ggtcgtgtcc gatccgcgtc tcgccgacaa tccgctgatc     120
gccatcaacc aggccttcac cgacctgacc ggctattccg aagaagaatg cgtcggccgc     180
aattgccgat tcctggcagg ttccggcacc gagccgtggc tgaccgacaa gatccgccaa     240
ggcgtgcgcg agcacaagcc ggtgctggtc gagatcctga actacaagaa ggacggcacg     300
ccgttccgca atgccgtgct cgttgcaccg atctacgatg acgacgacga gcttctctat     360
ttcctcggca gccaggtcga agtcgacgac gaccagccca acatgggcat ggcgcgccgc     420
gaacgcgccg cggaaatgct caggacgctg tcgccgcgcc agctcgaggt tacgacgctg     480
gtggcatcgg gcttgcgcaa caaggaagtg gcggcccggc tcggcctgtc ggagaaaacc     540
gtcaagatgc accgcgggct ggtgatggaa aagctcaacc tgaagaccag cgccgatctg     600
gtgcgcattg ccgtcgaagc cggaatctaa                                     630

<210> SEQ ID NO 73
<211> LENGTH: 209
<212> TYPE: PRT
<213> ORGANISM: Erythrobacter litoralis

<400> SEQUENCE: 73

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
            20                  25                  30

Arg Leu Ala Asp Asn Pro Leu Ile Ala Ile Asn Gln Ala Phe Thr Asp
        35                  40                  45

Leu Thr Gly Tyr Ser Glu Glu Cys Val Gly Arg Asn Cys Arg Phe
    50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
            100                 105                 110

Asp Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
    130                 135                 140
```

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile

<210> SEQ ID NO 74
<211> LENGTH: 209
<212> TYPE: PRT
<213> ORGANISM: Artificial sequence
<220> FEATURE:
<223> OTHER INFORMATION: EL222 mutant

<400> SEQUENCE: 74

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
            20                  25                  30

Arg Leu Ala Asp Asn Pro Leu Ile Ala Ile Asn Gln Ala Phe Thr Asp
        35                  40                  45

Leu Thr Gly Tyr Ser Glu Glu Glu Cys Val Gly Arg Asn Cys Arg Phe
    50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
            100                 105                 110

Asp Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
    130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile

<210> SEQ ID NO 75
<211> LENGTH: 209
<212> TYPE: PRT
<213> ORGANISM: Artificial sequence
<220> FEATURE:
<223> OTHER INFORMATION: EL222 mutant

<400> SEQUENCE: 75

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
            20                  25                  30

Arg Leu Ala Asp Asn Pro Ile Ile Ala Ile Asn Gln Ala Phe Thr Asp
        35                  40                  45

Leu Thr Gly Tyr Ser Glu Glu Cys Val Gly Arg Asn Cys Arg Phe
    50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
                100                 105                 110

Asp Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
            195                 200                 205

Ile

<210> SEQ ID NO 76
<211> LENGTH: 209
<212> TYPE: PRT
<213> ORGANISM: Artificial sequence
<220> FEATURE:
<223> OTHER INFORMATION: EL222 mutant

<400> SEQUENCE: 76

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
            20                  25                  30

Arg Leu Ala Asp Asn Pro Leu Ile Ala Ile Asn Gln Ala Phe Thr Asp
        35                  40                  45

Leu Thr Gly Tyr Ser Glu Glu Cys Val Gly Arg Asn Cys Arg Phe
    50                  55                  60

Leu Gln Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
                100                 105                 110

Asp Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu

```
                     165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile

<210> SEQ ID NO 77
<211> LENGTH: 209
<212> TYPE: PRT
<213> ORGANISM: Artificial sequence
<220> FEATURE:
<223> OTHER INFORMATION: EL222 mutant

<400> SEQUENCE: 77

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
            20                  25                  30

Arg Leu Ala Asp Asn Pro Leu Ile Ala Ile Asn Gln Ala Phe Thr Asp
        35                  40                  45

Leu Thr Gly Tyr Ser Glu Glu Glu Cys Val Gly Arg Asn Cys Arg Phe
    50                  55                  60

Leu Arg Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
            100                 105                 110

Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
    130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile

<210> SEQ ID NO 78
<211> LENGTH: 209
<212> TYPE: PRT
<213> ORGANISM: Artificial sequence
<220> FEATURE:
<223> OTHER INFORMATION: EL222 mutant

<400> SEQUENCE: 78

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
            20                  25                  30

Arg Leu Ala Asp Asn Pro Leu Ile Ala Ile Asn Gln Ala Phe Thr Asp
        35                  40                  45
```

```
Leu Thr Gly Tyr Ser Glu Glu Glu Cys Val Gly Arg Asn Cys Arg Phe
 50                  55                  60

Leu Thr Gly Ser Gly Thr Glu Pro Trp Leu Thr Asp Lys Ile Arg Gln
 65              70                  75                  80

Gly Val Arg Glu His Lys Pro Val Leu Val Glu Ile Leu Asn Tyr Lys
                 85                  90                  95

Lys Asp Gly Thr Pro Phe Arg Asn Ala Val Leu Val Ala Pro Ile Tyr
            100                 105                 110

Asp Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
            195                 200                 205

Ile

<210> SEQ ID NO 79
<211> LENGTH: 209
<212> TYPE: PRT
<213> ORGANISM: Artificial sequence
<220> FEATURE:
<223> OTHER INFORMATION: EL222 mutant

<400> SEQUENCE: 79

Gly Ala Asp Asp Thr Arg Val Glu Val Gln Pro Pro Ala Gln Trp Val
 1               5                  10                  15

Leu Asp Leu Ile Glu Ala Ser Pro Ile Ala Ser Val Val Ser Asp Pro
                 20                  25                  30

Arg Leu Ala Asp Asn Pro Leu Ile Ala Ile Asn Gln Ala Phe Thr Asp
             35                  40                  45

Leu Thr Gly Tyr Ser Glu Glu Glu Cys Val Gly Arg Asn Cys Arg Phe
 50                  55                  60

Leu Ala Gly Ser Gly Thr Glu Pro Trp Leu Thr Asp Lys Ile Arg Gln
 65              70                  75                  80

Gly Val Arg Glu His Lys Pro Val Leu Val Glu Ile Leu Asn Tyr Lys
                 85                  90                  95

Lys Asp Gly Thr Pro Phe Arg Asn Ala Val Leu Ile Ala Pro Ile Tyr
            100                 105                 110

Asp Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190
```

Asn Leu Lys Thr Ser Ala Asp Leu Val Arg Ile Ala Val Glu Ala Gly
        195                 200                 205

Ile

<210> SEQ ID NO 80
<211> LENGTH: 209
<212> TYPE: PRT
<213> ORGANISM: Artificial sequence
<220> FEATURE:
<223> OTHER INFORMATION: EL222 mutant

<400> SEQUENCE: 80

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
            20                  25                  30

Arg Leu Ala Asp Asn Pro Ile Ile Ala Ile Asn Gln Ala Phe Thr Asp
        35                  40                  45

Leu Thr Gly Tyr Ser Glu Glu Cys Val Gly Arg Asn Cys Arg Phe
    50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
            100                 105                 110

Asp Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile

<210> SEQ ID NO 81
<211> LENGTH: 209
<212> TYPE: PRT
<213> ORGANISM: Artificial sequence
<220> FEATURE:
<223> OTHER INFORMATION: EL222 mutant

<400> SEQUENCE: 81

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
            20                  25                  30

Arg Leu Ala Asp Asn Pro Leu Ile Ala Ile Asn Gln Ala Phe Thr Asp
        35                  40                  45

Leu Thr Gly Tyr Ser Glu Glu Cys Val Gly Arg Asn Cys Arg Phe
    50                  55                  60

Leu Gln Gly Ser Gly Thr Glu Pro Trp Leu Thr Asp Lys Ile Arg Gln

```
                 65                  70                  75                  80
Gly Val Arg Glu His Lys Pro Val Leu Val Glu Ile Leu Asn Tyr Lys
                 85                  90                  95

Lys Asp Gly Thr Pro Phe Arg Asn Ala Val Leu Val Ala Pro Ile Tyr
            100                 105                 110

Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
            195                 200                 205

Ile

<210> SEQ ID NO 82
<211> LENGTH: 209
<212> TYPE: PRT
<213> ORGANISM: Artificial sequence
<220> FEATURE:
<223> OTHER INFORMATION: EL222 mutant

<400> SEQUENCE: 82

Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
                20                  25                  30

Arg Leu Ala Asp Asn Pro Leu Ile Ala Ile Asn Gln Ala Phe Thr Asp
            35                  40                  45

Leu Thr Gly Tyr Ser Glu Glu Glu Cys Val Gly Arg Asn Cys Arg Phe
50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Ile Ala Pro Ile Tyr
            100                 105                 110

Asp Asp Asp Asp Glu Leu Leu Tyr Phe Leu Gly Ser Gln Val Glu Val
            115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
            195                 200                 205

Ile
```

<210> SEQ ID NO 83
<211> LENGTH: 209
<212> TYPE: PRT
<213> ORGANISM: Artificial sequence
<220> FEATURE:
<223> OTHER INFORMATION: EL222 mutant

<400> SEQUENCE: 83

```
Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Val Val Ser Asp Pro
                20                  25                  30

Arg Leu Ala Asp Asn Pro Ile Ile Ala Ile Asn Gln Ala Phe Thr Asp
            35                  40                  45

Leu Thr Gly Tyr Ser Glu Glu Glu Cys Val Gly Arg Asn Cys Arg Phe
        50                  55                  60

Leu Gln Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Val Ala Pro Ile Tyr
            100                 105                 110

Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
            180                 185                 190

Asn Leu Lys Thr Ser Ala Asp Leu Val Arg Ile Ala Val Glu Ala Gly
        195                 200                 205

Ile
```

<210> SEQ ID NO 84
<211> LENGTH: 209
<212> TYPE: PRT
<213> ORGANISM: Artificial sequence
<220> FEATURE:
<223> OTHER INFORMATION: EL222 mutant

<400> SEQUENCE: 84

```
Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
                20                  25                  30

Arg Leu Ala Asp Asn Pro Ile Ile Ala Ile Asn Gln Ala Phe Thr Asp
            35                  40                  45

Leu Thr Gly Tyr Ser Glu Glu Glu Cys Val Gly Arg Asn Cys Arg Phe
        50                  55                  60

Leu Ala Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95
```

```
Lys Asp Gly Thr Pro Phe Arg Asn Ala Val Leu Ile Ala Pro Ile Tyr
            100                 105                 110

Asp Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
                180                 185                 190

Asn Leu Lys Thr Ser Ala Asp Leu Val Arg Ile Ala Val Glu Ala Gly
            195                 200                 205

Ile
```

<210> SEQ ID NO 85
<211> LENGTH: 209
<212> TYPE: PRT
<213> ORGANISM: Artificial sequence
<220> FEATURE:
<223> OTHER INFORMATION: EL222 mutant

<400> SEQUENCE: 85

```
Gly Ala Asp Asp Thr Arg Val Glu Val Gln Pro Pro Ala Gln Trp Val
1               5                   10                  15

Leu Asp Leu Ile Glu Ala Ser Pro Ile Ala Ser Ile Val Ser Asp Pro
            20                  25                  30

Arg Leu Ala Asp Asn Pro Ile Ile Ala Ile Asn Gln Ala Phe Thr Asp
        35                  40                  45

Leu Thr Gly Tyr Ser Glu Glu Glu Cys Val Gly Arg Asn Cys Arg Phe
    50                  55                  60

Leu Gln Gly Ser Gly Thr Glu Pro Trp Leu Thr Asp Lys Ile Arg Gln
65                  70                  75                  80

Gly Val Arg Glu His Lys Pro Val Leu Val Glu Ile Leu Asn Tyr Lys
                85                  90                  95

Lys Asp Gly Thr Pro Phe Arg Asn Ala Val Leu Ile Ala Pro Ile Tyr
            100                 105                 110

Asp Asp Asp Asp Glu Leu Leu Tyr Phe Leu Gly Ser Gln Val Glu Val
        115                 120                 125

Asp Asp Asp Gln Pro Asn Met Gly Met Ala Arg Arg Glu Arg Ala Ala
        130                 135                 140

Glu Met Leu Arg Thr Leu Ser Pro Arg Gln Leu Glu Val Thr Thr Leu
145                 150                 155                 160

Val Ala Ser Gly Leu Arg Asn Lys Glu Val Ala Ala Arg Leu Gly Leu
                165                 170                 175

Ser Glu Lys Thr Val Lys Met His Arg Gly Leu Val Met Glu Lys Leu
                180                 185                 190

Asn Leu Lys Thr Ser Ala Asp Leu Val Arg Ile Ala Val Glu Ala Gly
            195                 200                 205

Ile
```

BLUE-LIGHT INDUCIBLE SYSTEM FOR GENE EXPRESSION

CROSS REFERENCE TO RELATED APPLICATIONS

This application is a 371 National Stage Entry of PCT/US2012/065493, filed Nov. 16, 2012, which claims the priority of U.S. Provisional Application Ser. No. 61/561,585, filed on Nov. 18, 2011, the entire disclosure of which is incorporated herein by reference.

GOVERNMENT INTEREST

This invention was made with United States government support under grant number R01 GM081875 awarded by the National Institutes of Health. The United States government has certain rights in the invention.

INCORPORATION OF SEQUENCE LISTING

The sequence listing that is contained in the file named "UTSW004WO_ST25.txt", which is 44 kilobytes as measured in Microsoft Windows operating system and was created on Nov. 15, 2012, is filed electronically herewith and incorporated herein by reference.

BACKGROUND OF THE INVENTION

I. Field of the Invention

The present invention relates generally to the field of molecular biology. More specifically, the invention relates to methods and compositions regarding light-responsive proteins and nucleic acids for gene expression.

II. Related Art

The ability to artificially control gene expression in eukaryotic cells is essential for many applications in basic molecular biology, including cell biology, biochemical or biomedical research. Most currently available gene regulatory systems are based on chemical inducer molecules (e.g. tetracycline) that must enter a cell to bind a target protein and activate its transcriptional activity. Such systems generally have downsides that include the need for the addition of a small chemical inducer and typically an inability to turn gene expression on and off rapidly.

SUMMARY OF THE INVENTION

In one aspect, the invention provides a recombinant nucleic acid molecule comprising a sequence encoding a light responsive DNA binding protein (LRDP) comprising: a) a LOV domain; and b) a DNA binding domain (DBD), wherein said LOV domain and DBD are from a homologous species, and wherein said sequence encoding said LRDP is operatively linked to a polynucleotide encoding a heterologous transcriptional activation domain. In one embodiment, the LRDP is an EL222-LOV LRDP.

In another aspect, the invention provides a polypeptide encoded by a nucleic acid molecule of the present invention, for instance comprising a sequence encoding a LRDP, wherein the LRDP comprises a LOV domain and a DNA binding domain from a homologous species operatively linked to a polynucleotide encoding a heterologous transcription activation domain. In a particular aspect, the invention provides a cell comprising such a polypeptide.

In yet another aspect, the invention provides a recombinant nucleic acid molecule comprising an EL222-binding consensus sequence operably linked to a heterologous transcribable polynucleotide sequence. In one embodiment, the DNA binding site comprises a sequence selected from the group consisting of SEQ ID NOs: 4-66. In yet another embodiment, the transcribable polynucleotide sequence operably linked to the EL222-binding consensus sequence is selected from the group consisting of a reporter sequence, a cell stress tolerance sequence, an industrial enzyme encoding sequence, a sequence encoding a biofuel production enzyme, a sequence encoding a cell lysis protein, and a sequence encoding a cell regulatory protein.

In still another aspect, the invention provides a cell comprising a recombinant nucleic acid molecule of the invention comprising an EL222-binding consensus sequence operably linked to a heterologous transcribable polynucleotide.

Also provided by the invention is a cell or multicellular organism comprising a nucleic acid molecule of the invention comprising a LRDP encoding sequence comprising a LOV domain and a DNA binding domain from a homologous species operatively linked to a polynucleotide encoding a heterologous transcription activation domain. In one embodiment, such a cell or multicellular organism of the invention further comprises a recombinant nucleic acid molecule comprising an EL222 binding consensus sequence operably linked to a heterologous transcribable polynucleotide sequence. In another embodiment, a cell or multicellular organism of the invention may also comprise a second nucleic acid molecule comprising a DNA binding site for said DNA binding domain operably linked to a heterologous transcribable polynucleotide sequence. In certain embodiments, a cell or multicellular organism of the present invention may be selected from the group consisting of a bacterial cell, yeast cell, animal cell, mammalian cell, insect cell, fungal cell and plant cell.

In a particular aspect, the invention provides a method of activating transcription in a cell comprising illuminating a cell of the invention with blue light. In one embodiment, transcription in the cell is activated by at least 10×, 11×, 12×, 13×, 14×, 15×, 16×, 17×, 18×, 19×, 20×, 21×, 22×, 23×, 24×, 25×, 30×, 35×, 40×, 45×, 50×, 55×, 60×, 65×, 70×, 75×, 80×, 85×, 90×, 95×, 100×, 105× or 110× relative to transcription in the absence of blue light. In another aspect, the invention provides a method of inactivating blue-light induced transcription comprising diminishing blue light exposure to a cell of the invention.

In one aspect, the present invention provides a method of identifying high-affinity DNA binding sites for a light responsive DNA binding protein (LRDP) comprising a LOV domain and a DNA binding domain (DBD), wherein said LOV domain and DBD are from a homologous species, wherein said method comprises: a) incubating a polypeptide comprising a LOV domain and said DNA binding domain with a plurality of different polynucleotide sequences in the presence of blue light; b) removing said blue light; and c) identifying polynucleotide sequences bound to said DNA binding domain in the presence of blue light and released from said DNA binding domain in the absence of blue light, wherein said identifying comprises isolating and sequencing said polynucleotide sequences bound to said DNA binding domain in the presence of blue light and released from said DNA binding domain in the absence of blue light, whereby a high-affinity DNA binding site is identified. In one embodiment, the plurality of different polynucleotide sequences are distributed on an array and said identifying comprises determining the identity of said polynucleotide sequences bound to said DNA binding domain in the presence of blue light and released from said DNA binding domain in the absence of blue light on said array. In another embodiment, the polypeptide is immobilized on a surface. In yet another embodiment, the LRDP used in the above method comprises at least one LRDP variant and/or may be operably linked to a detection moiety. Such detection moieties may be selected from the group consisting of isotopic label and optically detectable label, such as a fluorescent protein, green fluorescent protein variants or enzymatic labels. In another embodiment, the LRDP comprises a sequence encoding an EL222 LRDP variant comprising altered blue light responsiveness as compared to wild-type EL222 LRDP.

In another aspect, the invention provides a method of recruiting proteins to a surface in a light dependent manner comprising: a) coating the surface with DNA-binding sequence molecules; b) exposing the surface to a light responsive DNA binding protein (LRDP); and c) exposing the surface to blue light. In one embodiment, the LRDP of the above method may be linked to a second polypeptide. Said method may optionally further comprise the step of d) detecting the second polypeptide. In certain embodiments, the second polypeptide may be linked to a detection moiety, for instance, an isotopic label or optically detectable label, such as a green fluorescent protein, green fluorescent protein variants and enzymatic labels. In another embodiment, the DNA-binding sequence molecules may comprise distinct variant sequences and/or may be coated onto the surface at discrete locations. In yet another embodiment, the LRDP of the above method comprises at least one LRDP variant.

In yet another aspect, the present invention provides a method of light dependent isolation of target moieties comprising: a) inserting into the genome of cell a DNA binding site for a LRDP; b) extracting said genome from said cell or progeny thereof; c) applying said extracted genome to immobilized LRDP in the presence of blue light, whereby said target moieties are isolated. In one embodiment, the target moieties of such a method are selected from the group consisting of genomic fragments and DNA binding proteins.

In a still another embodiment, the invention provides a method of altering expression of a polynucleotide in a subpopulation of cells comprising illuminating with blue light a discrete number of cells of the invention, for instance cells comprising a nucleotide of the invention comprising a LRDP encoding sequence comprising a LOV domain and a DNA binding domain from a homologous species operatively linked to a polynucleotide encoding a heterologous transcription activation domain, whereby the discrete number of cells exhibit altered gene expression. In one embodiment, the method further comprises ceasing said illuminating, whereby said expression reverts to baseline.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Demonstrates light-inducible transgene expression in HEK293T cells using VP16-EL222. Panel "a" shows expression results for a Firefly luciferase reporter construct under the control of 5 copies of 45 bp Clone-1 sequence (SEQ ID NO:68) co-transfected with the VP16-EL222 expression construct into HEK293T cells. Panel "b" shows expression results for a Firefly luciferase reporter construct under the control of 5 copies of 20-bp C1-2 (SEQ ID NO:69) sequence similarly co-transfected with the VP16-EL222 expression construct into HEK293T cells. One day post-transfection, the cells were kept in the dark or illuminated with blue light for 24 hr. Afterwards, cells were harvested and luciferase activity was measured (left graph). Luciferase values were normalized for transfection variability using a control *Renilla* luciferase reporter with a constitutively-active CMV promoter and was co-transfected with the Firefly luciferase reporter and VP16-EL222 expression vector. The change in transcription is expressed as a fold change (FC) in activation, where FC=[(Firefly/*Renilla*)$_{VP16\text{-}EL222}$/(Firefly/*Renilla*)$_{empty\ vector}$]. The regulatory DNA sequence for each reporter construct is shown, the EL 222-DBS is represented in upper case letters and the linker region connecting each EL222-DBS is represented in lower case letters. The 20 bp region that corresponds to the C1-2 sequence is shown in bold. Data are shown as the mean and the standard error from n=2 (pClone1-45[Luc]) or n=3 (pClone1-20[Luc]) independent experiments each done in triplicate.

*nilla*)$_{empty\ vector}$]. Data are shown as the mean and the standard error from n=3 independent experiments each done in triplicate.

FIG. 6. Shows the nucleotide sequence encoding the NLS-VP16-EL222 (14-222) (SEQ ID NO:70). Nucleotides 7-27, shown in italics and underlined, corresponds to the region encoding the nuclear localization signal (NLS); nucleotides 28-261, shown in bold, correspond to the region encoding VP16; and nucleotides 268-879, shown as boxed, correspond to the region encoding the EL222 (14-222) LOV-DNA binding domain.

FIG. 7. Shows that proper transcriptional activation in HEK293T cells requires both high affinity DNA binding site and blue light illumination. Panel "a" demonstrates DNA binding site specificity, showing results from cells that were co-transfected with VP16 (empty) or VP16-EL222 and a reporter construct containing either 5 copies of the 20-bp C1-2 sequence (SEQ ID NO: 69), 3 copies of the AN-45 sequence or 5 copies of the upstream activation sequence from the Gal4 gene (UAS$_G$). Cells were kept in the dark or illuminated with blue light pulses (20 s ON 60 s OFF; 2 W/m$^2$) for 24 hr. Panel "b" demonstrates that illumination with red light does not result in transcriptional activation.

Figure 8:
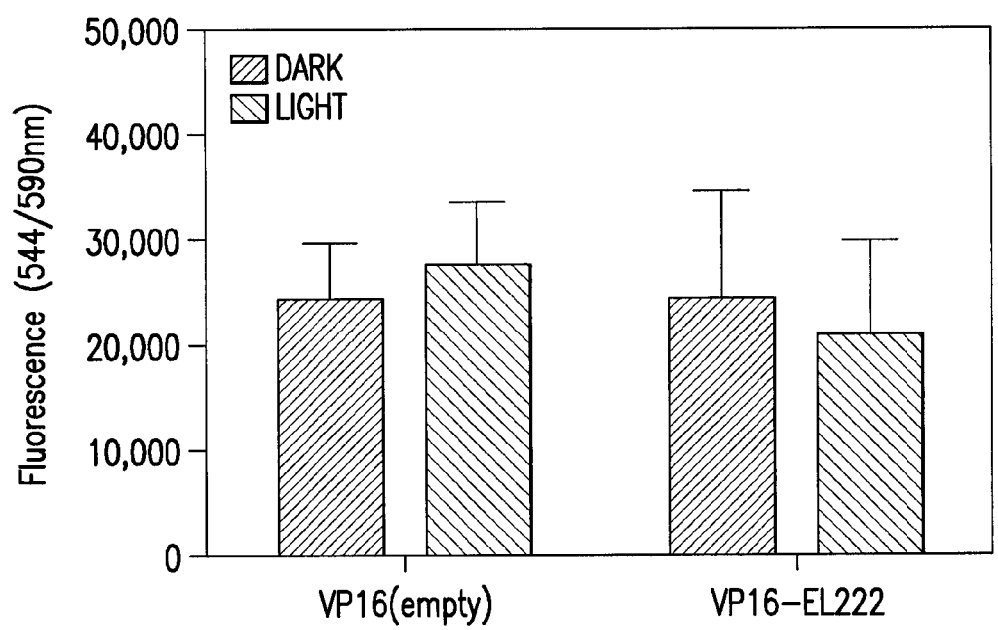

FIG. 8. Shows that illumination with blue light to activate the light responsive DNA binding protein (LRDP) has no significant negative impact on HEK293T cell viability.

Figure 9A:
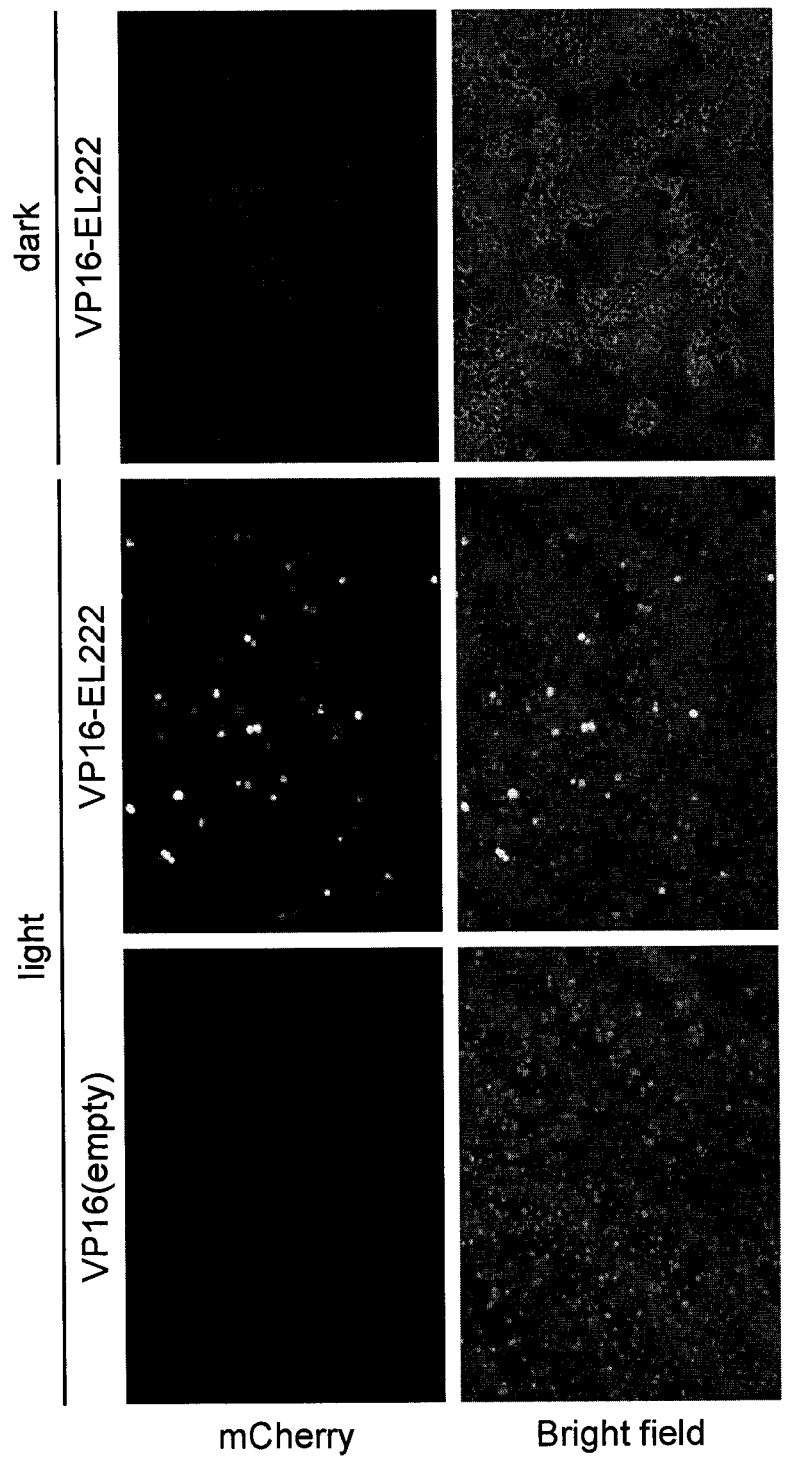

FIG. 9. Shows visualization of VP16-EL222-driven mCherry fluorescence in HEK293T cells. Panel "a" shows cells that were transiently transfected with vectors to co-express VP16 (empty) or VP16-E222 and an mCherry reporter under the control of 5 copies of the 20 bp C2-1 sequence (SEQ ID NO: 69). Cells were kept in the dark or illuminated with blue light pulses (20 s ON, 60 s OFF; 2 W/m$^2$) for 24 hr prior to imaging on fluorescence microscope (10× magnification; 3 s exposure). Panel "b" shows surface plot representations (done using ImageJ) of the results described in panel "a."

Figure 10A:
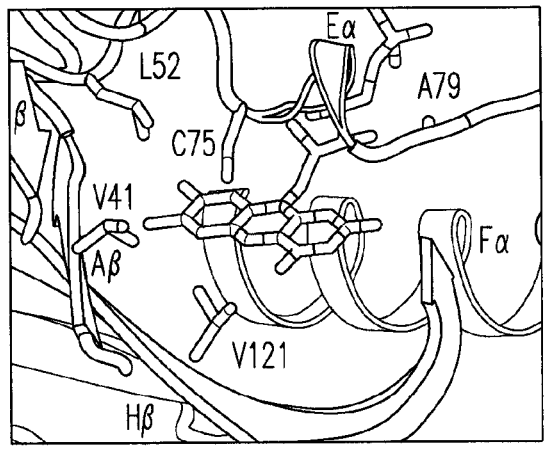
Figure 10B:
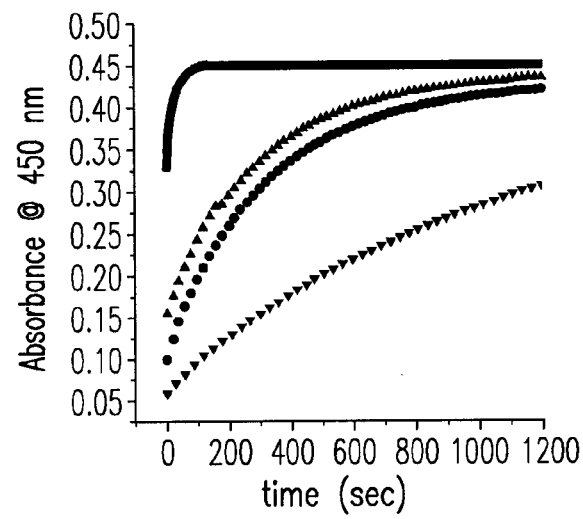
Figure 10C:
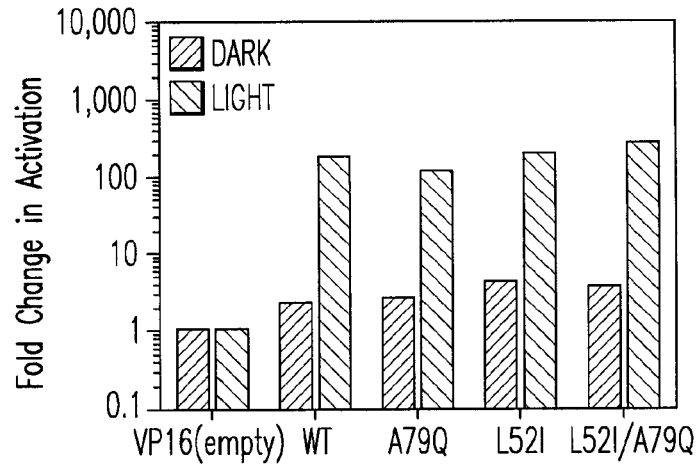

FIG. 10. Demonstrates that active site variants of EL222 extend the lifetime of the light-state adduct. Panel "a" shows mutations in EL222 that alter the rate of activation of the protein localized to the active site as indicated in the crystal structure for EL222 (Nash et al., *PNAS* 108 (2011): 9449). Panel "b" demonstrates that EL222 variants tune the lifetime of the adduct state relative to WT (top line, τ~30 s). V41I:V121I (third line from the top) and A79Q (second line from the top) both increase the lifetime of the adduct state 10-fold. Combining these mutations with a further V52I variation increases the lifetime to a maximum of τ~2000 s in a V41I/V52I/A79Q/V121I (AQTrip, bottom line) variant. The rate of dark-state recovery of the proteins was determined by fitting the UV-visible absorbance spectra of EL222 at 450 nm after illumination to first-order exponential curves (Zoltowski BD and Gardner KH; unpublished results). Panel c shows the calculated fold change in activation (see FIG. 4) for VP16 fusion proteins of the A79Q, L52I, L52I/A79Q variants, made and co-transfected with the 5×20 bp C2-1 (SEQ ID NO: 69) Luciferase reporter construct into HEK293T cells.

Figure 5:
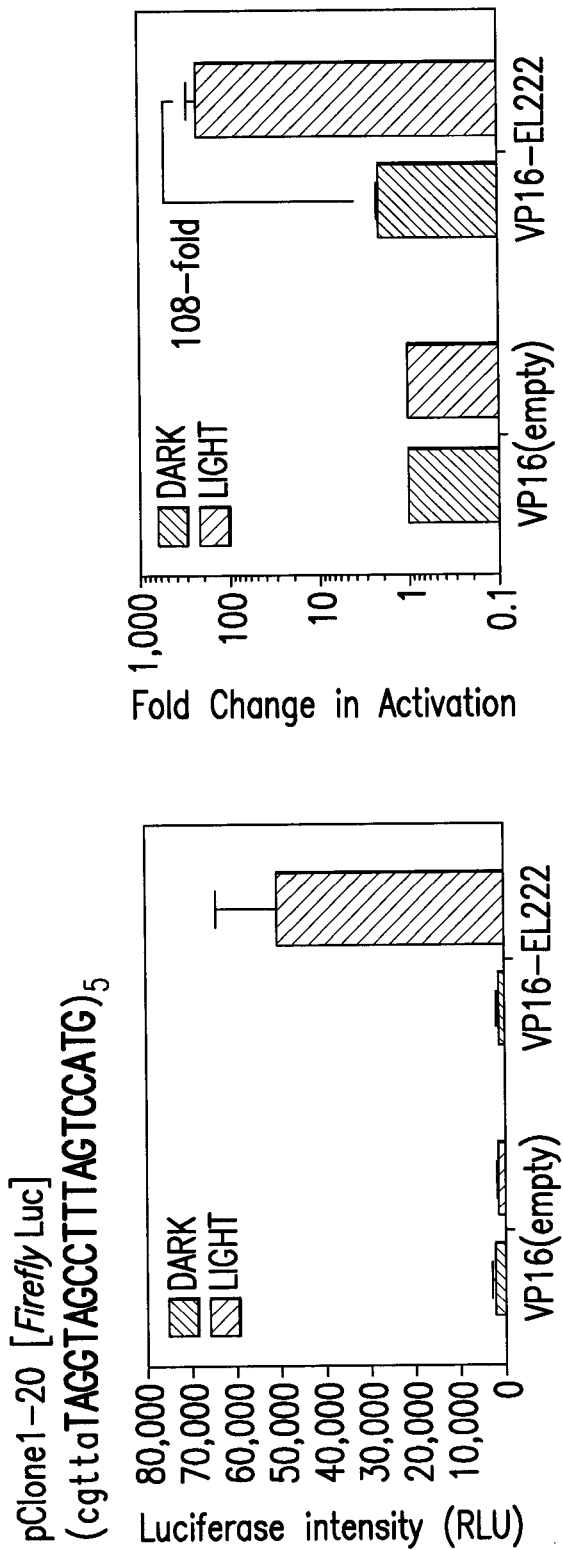
FIG. 5. Demonstrates improved effects on gene expression in HEK293T cells using illumination protocols optimized for the lifetime of the wildtype EL222 photoexcited state using an illumination schedule of (20 s light:60 s dark=20 s ON, 60 s OFF) through a 24 hr period. The figure shows expression results for a Firefly luciferase reporter construct under the control of 5 copies of 20-bp C1-2 (SEQ ID NO:69) sequence co-transfected with the VP16-EL222 expression construct into HEK293T cells. The change in transcription is expressed as a fold change (FC) in activation, where FC=[(Firefly/*Renilla*)$_{VP16\text{-}EL222}$/(Firefly/*Re-*

FIG. 11. Shows results from a cell line that stably expresses VP16-EL222 and shows higher reporter activation. Panel "a" shows Luciferase activity for Clone-3 and HEK293T cells that were transfected with a vector containing 20 bp C2-1 sequence (SEQ ID NO: 69) only (see FIG. 5) and illuminated with blue-light pulses (20 s ON, 60 s OFF) or kept in the dark for 3, 6, 9, 12 and 24 hr before cells were harvested. Panel "b" also shows Luciferase activity as in panel "a" except cells were illuminated with blue-light pulses of 20 s ON 60 s OFF, 10 s ON 70 s OFF, or 5 s ON, 75 s OFF, for 12 hr post-transfection. Panel c shows western blot results for Clone-3 (+VP16-EL222) and HEK293T (−VP16-EL222) cells transfected with the 5×20 bp C2-1 (SEQ ID NO: 69) Luciferase reporter and illuminated with blue-light pulses (10 s ON, 70 s OFF) for 12 hr or kept in the dark. Cells lysates were made from untransfected cells (unt) and cells from each condition (+ or −VP16-EL222), these were blotted with antibodies against Firefly Luciferase or β-actin (loading control). The asterisk indicates a non-specific band detected by the anti-Luciferase antibody.

Figure 12A:
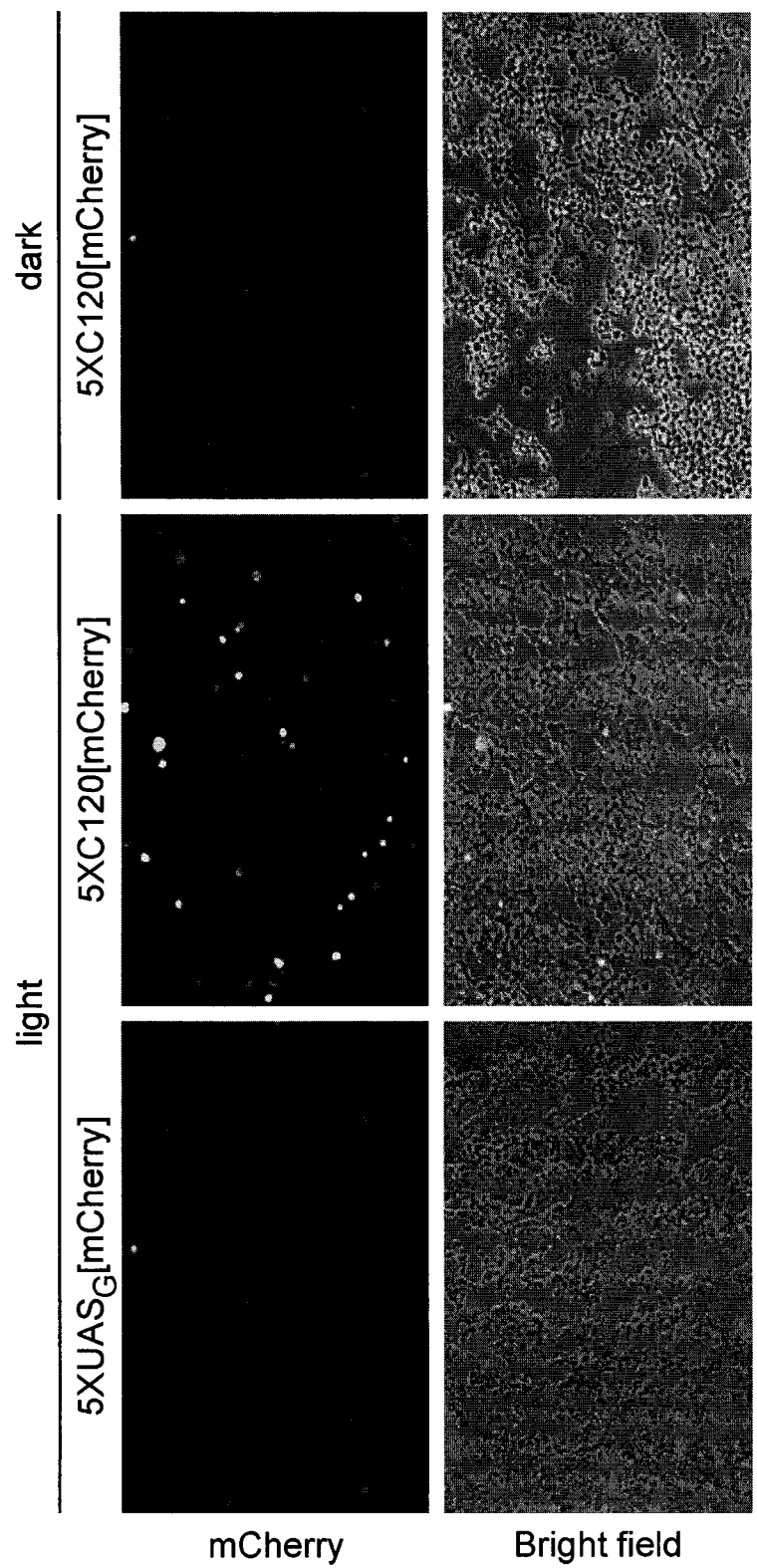
Figure 12B:
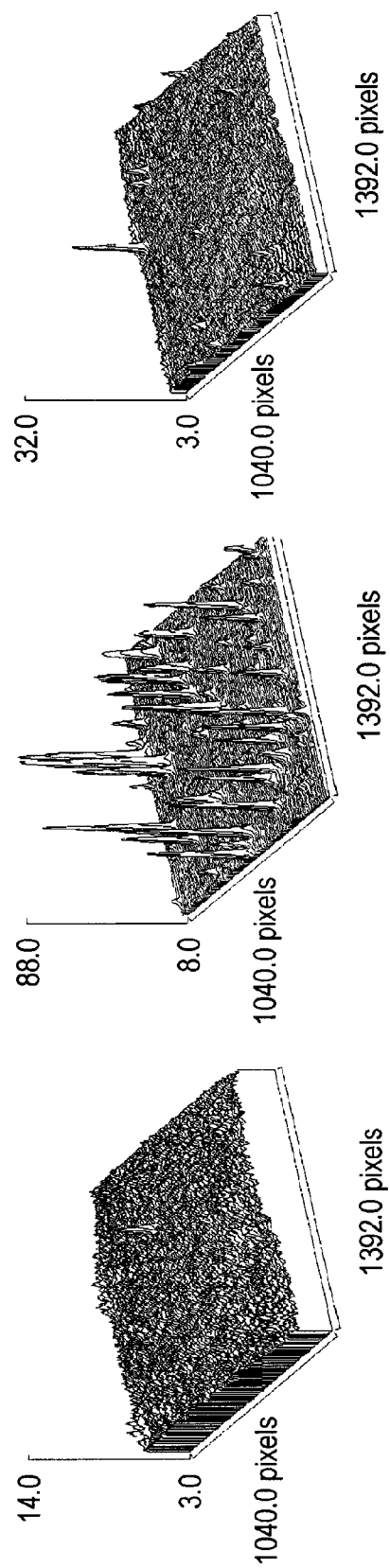

FIG. 12. Shows visualization of VP16-EL222-driven mCherry fluorescence in cells stably expressing VP16-EL222. Panel "a" shows cells transfected with an mCherry reporter under the control of either 5 copies of the 20 bp C2-1 sequence (SEQ ID NO: 69) or 5 copies of the UAS$_G$ sequence as control. Cells were kept in the dark or illuminated with blue light pulses (20 s ON, 60 s OFF; 2 W/m$^2$) for 24 hr prior to imaging on fluorescence microscope (10× magnification; 3 s exposure). Panel "b" shows surface plot representations (done using ImageJ) of the results described for panel "a."

Figure 13A:
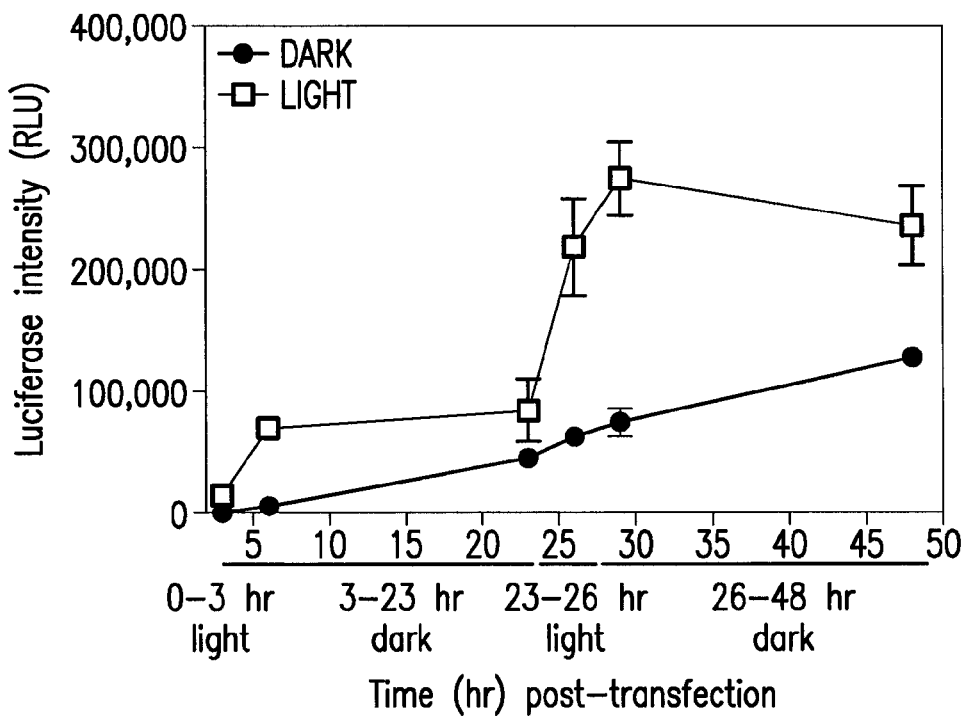
Figure 13B:
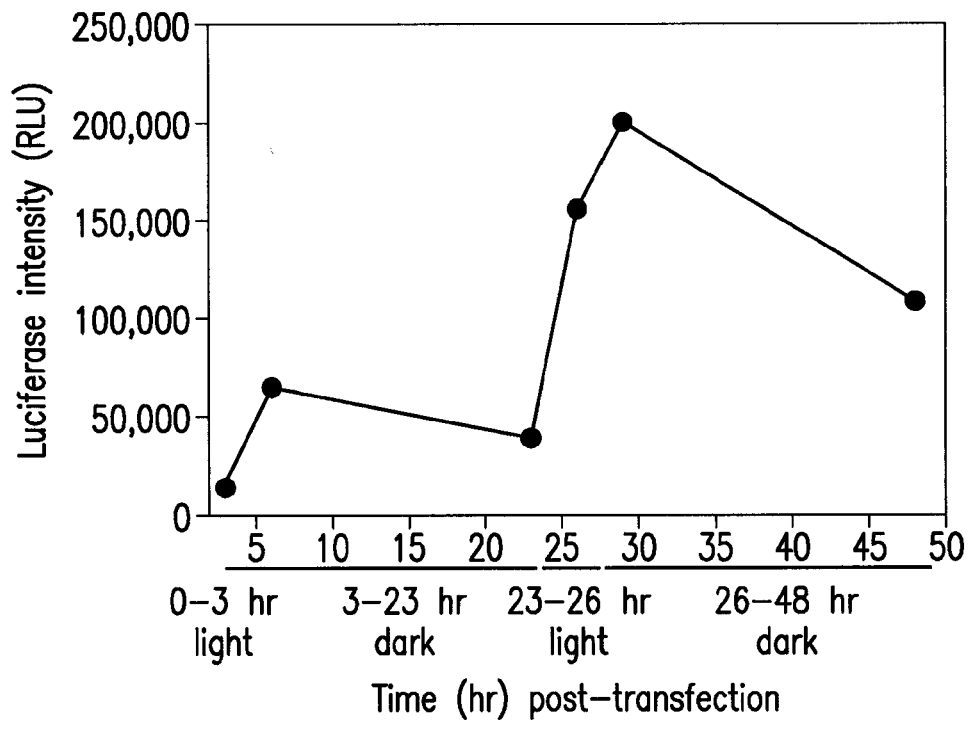

FIG. 13. Demonstrates transcriptional activation by VP16-EL222 is reversible and repeatable. Panel "a" shows results for Clone-3 cells that were transfected with the 5×20 bp C2-1 (SEQ ID NO: 69) Luciferase reporter and either incubated in the dark for the entire experiment (black line) or illuminated with blue-light pulses (20 s ON, 60 s OFF) for two separate 3-hour periods (grey line). Panel "b" shows normalized values, for which the luciferase intensity values obtained for the dark-state condition samples were subtracted from the light-state condition values.

BRIEF DESCRIPTION OF THE SEQUENCE LISTING

SEQ ID NO:1—The single-stranded oligonucleotide used for the SELEX procedure.

SEQ ID NO:2—The forward L1 primer used to amplify DNA pool for SELEX procedure.

SEQ ID NO:3—The reverse L1 primer used to amplify DNA pool for SELEX procedure.

SEQ ID NO:4-SEQ ID NO:10—Seven DNA-binding site sequences recognizing the EL222 DNA-binding domain identified through the SELEX procedure and chosen for follow up studies.

SEQ ID NO:11-SEQ ID NO:62—The remaining DNA-binding site sequences recognizing the EL222 DNA-binding domain identified through the SELEX procedure.

SEQ ID NO:63-SEQ ID NO:66—Four overlapping 20 bp Clone-1 derived sequences for further study (C1-1 through C1-4).

SEQ ID NO:67—The consensus EL222 binding motif sequence.

SEQ ID NO:68—The 45 bp pClone1-45 sequence comprising the 33-bp randomized region flanked by 6 bp of primer binding sequence.

SEQ ID NO:69—The 20-bp pClone1-20 sequence comprising the Clone-1 derived C1-2 sequence and linker sequence.

SEQ ID NO:70—The nucleotide sequence encoding the VP16-NLS-EL222 fusion protein.

SEQ ID NO:71—The VP16-NLS-EL222 fusion protein sequence.

SEQ ID NO:72—The nucleotide sequence encoding the 13-residue N-terminal truncation of WT-EL222.

SEQ ID NO:73—The 13-residue N-terminal truncation of WT-EL222 amino acid sequence.

SEQ ID NO:74—The EL222 V41I variant amino acid sequence.

SEQ ID NO:75—The EL222 L52I variant amino acid sequence.

SEQ ID NO:76—The EL222 A79Q variant amino acid sequence.

SEQ ID NO:77—The EL222 A79R variant amino acid sequence.

SEQ ID NO:78—The EL222 A79T variant amino acid sequence.

SEQ ID NO:79—The EL222 V121I variant amino acid sequence.

SEQ ID NO:80—The EL222 V41I:L52I variant amino acid sequence.

SEQ ID NO:81—The EL222 V41I:A79Q variant amino acid sequence.

SEQ ID NO:82—The EL222 V41I:V121I variant amino acid sequence.

SEQ ID NO:83—The EL222 L52I:A79Q variant amino acid sequence.

SEQ ID NO:84—The EL222 V41I:L52I:V121I variant amino acid sequence.

SEQ ID NO:85—The EL222 V41I:L52I:A79Q:V121I variant amino acid sequence.

DETAILED DESCRIPTION OF ILLUSTRATIVE EMBODIMENTS

The present invention provides a system for selectively and efficiently activating gene expression in a light-responsive manner. The present disclosure therefore provides methods, nucleic acid molecules, proteins, kits and assays related to light-dependent regulation of gene expression. The present invention provides in certain embodiments a light-responsive DNA-binding protein operably linked to a transcriptional activation domain that functions to bind DNA and activate transcription in response to blue light. In one embodiment, the light-responsive DNA-binding protein is a prokaryotic protein, such as a bacterial protein. In a specific embodiment, the protein is EL222 (E. litoralis 222 amino acid protein; Nash et al., Proc. Natl. Acad. Sci. 108 (2011): 9449; incorporated herein by reference). In another embodiment, the present invention provides DNA-binding sites capable of being recognized by a light-responsive DNA-binding protein of the invention. In a particular embodiment, such DNA-binding sites may be double stranded and thus DNA-binding sites represented as single stranded sequences herein may additionally comprise the complement thereof.

The present disclosure provides unique advantages over presently available gene expression systems. For instance, expression of only a single protein is sufficient in the system to directly activate transcription of a target gene in response to blue light. The light-responsive DNA-binding protein (LRDP) can be provided containing both a light-oxygen-voltage (LOV) domain and DNA-binding domain. Regulation of the DNA-binding ability of the light-responsive DNA-binding protein of the present invention can therefore be carried out within the same molecule as the DNA-binding protein, in other words, in cis, which can yield higher fold activation as compared to the presently available gene expression systems, such an at least 108-fold or greater up-regulation demonstrated in the Examples below.

In another embodiment, a light-responsive DNA-binding protein used herein is comprised as a single molecule without the need to artificially create a protein comprising both the light-responsive domain and the DNA-binding domain, such as a fusion protein. The light-responsive DNA-binding protein can then be operatively linked to a heterologous regulatory domain, such as one or more heterologous transcriptional activation domains. To the contrary, current photosensitive gene expression systems are designed as light-regulated "two-hybrid" type systems that associate separate DNA binding and gene activation components in a light-dependent manner.

The currently available light-dependent expression systems comprise additional limitations or complications overcome by the present invention. In particular, several light-dependent expression systems utilize a photosensitive protein requiring an unusual chromophore that must be exogenously provided for many different types of biologically-relevant host cells. The expression system of the present invention, however, relies on a commonly-available chromophore, flavin mononucleotide (FMN), eliminating the need to supply cells with exogenous small molecule precursors and/or engineer the expression of enzymes to promote the formation of such chromophores. Furthermore, the light-dependent expression systems currently available in the art are derived from eukaryotic sources increasing the potential for crosstalk and/or pleiotropic effects if utilized in hosts similar to the originating source. This crosstalk significantly limits the possibility of successful use in many biologically-relevant host cells, such as eukaryotic host cells. The light-responsive DNA-binding proteins of the present system, however, are uniquely derived from a lower organism, such as a prokaryotic organism, and thus may be effectively used for gene expression in cells of higher organisms, such as eukaryotic cells.

In certain embodiments, the gene expression system of the present invention uses blue light (400-480 nm) to trigger gene expression. The use of light as a control signal provides several advantages, as it can serve as a noninvasive, non-toxic, selective and rapid inducer. Importantly, many cells and tissues are not photoresponsive and therefore light is an ideal stimulus as it will not affect the physiology of most cell lines used in research. In addition, light allows for more precise spatial and temporal control of gene expression because it can be easily turned-on/off and be directed at a specific region or site in a cell, cell culture, tissue or organism. A key aspect of temporal control of such activation is that the photochemical signaling mechanism within a LOV domain shuts off quickly after illumination ceases as a photochemically-generated bond spontaneously cleaves. The rate of this cleavage can be modified using point mutations to residues near the chromophore binding site. In one embodiment, the present invention provides LOV domain sequences with such point mutations, for instance in the EL222 LOV domain. Thus, the use of light as a stimulus to control gene expression in vivo avoids nearly all of the drawbacks attributed to the inducing chemical or treatment of currently available systems.

In particular, most currently available gene regulatory systems are based on chemical inducer molecules (e.g. tetracycline) that must enter a cell to bind a target protein and activate its transcriptional activity. While these chemical-based systems are in widespread use, they have several key limitations, including: slow on/off times, difficulty in establishing well-defined spatial patterns of activation, and increased potential for off-target effects. Similar concerns can be raised about the effects of heat shock or other broad environmental changes as activating stimuli.

In one embodiment, the light-responsive DNA-binding protein of the invention comprises a light-responsive domain and DNA binding domain operably linked or connected to a transcriptional activation domain. In certain embodiments, the light-responsive domain and DNA binding domain are from a homologous species. In another embodiment, both domains may be from the same species or may be encoded from the same gene or a naturally contiguous nucleic acid molecule.

Light-responsive domains comprise protein domains that function in a light dependent manner, for instance, by changing structure in response to exposure to light. Light-responsive proteins and domains function in association with chromophores, which are moieties capable of detecting or capturing light energy. Any photosensory domain may be used as a light-responsive domain of the invention. In one embodiment the light-responsive domain is a LOV domain. LOV domains are light sensitive domains responsive to blue light that use a flavin mononucleotide, which is widely available in eukaryotic cells, as a chromophore. The LOV domain of the present invention may be any LOV domain known in the art. In one embodiment the LOV domain and the DNA binding domain of the invention are from a homologous species and have, for instance, co-evolved to naturally function as a contiguous protein or nucleic acid molecule. In a particular embodiment, the LOV domain of the present invention is a LOV domain from the E. litoralis 222 amino acid protein (EL222).

Figure 1A:
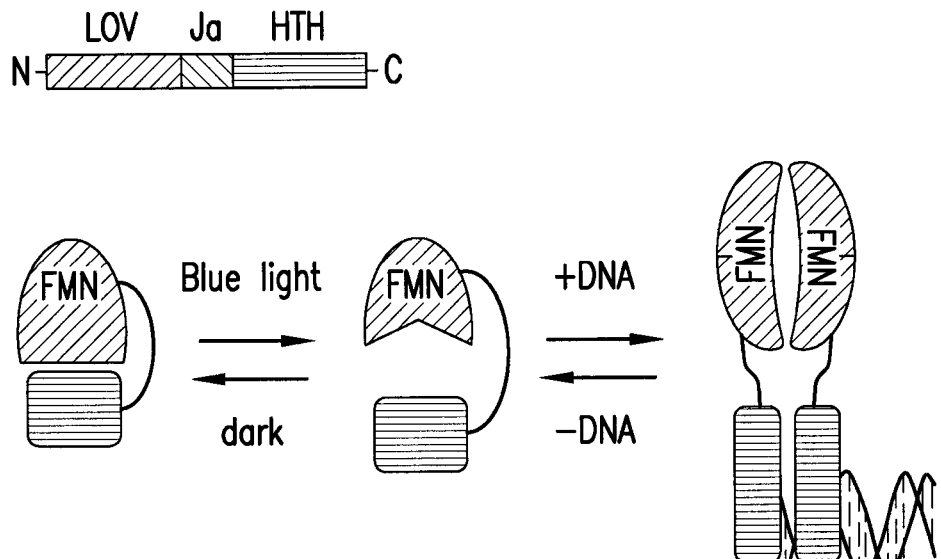
FIG. 1. Shows a model for the activation of the *E. litoralis* 222 amino acid protein (EL222) by blue light and the light-responsive EL222-based gene expression system. Panel "a" shows a schematic overview of EL222 architecture and signaling mechanism (Nash et al., 2011). Panel "b" demonstrates modification of EL222 for use in eukaryotic cells by adding a nuclear localization sequence (NLS) and a transcriptional activation domain (VP16-AD) from the herpes simplex virus VP16 protein. High affinity DNA binding sites (assembled in tandem repeats upstream of a minimal promoter) were also identified. In the dark, the VP16-EL222 chimera cannot activate a luciferase reporter construct under the control of five-tandem copies of EL222 DNA binding sites (EL222-DBS); exposure to blue light activates the VP16-EL222 protein allowing it to turn on luciferase transcription.

The EL222 protein consists of a photosensory (LOV) domain, an interdomain linker (J$\alpha$-helix), and a helix-turn-helix (HTH) DNA binding domain (FIG. 1a). In the dark, the LOV domain binds the HTH domain via interactions of its $\beta$-sheet with the HTH 4$\alpha$-helix. The HTH 4$\alpha$-helix typically provides a dimerization interface for DNA-bound HTH domains (FIG. 1a). Illumination with blue light triggers a photochemical reaction between the LOV domain and its flavin chromophore that leads to conformational changes that disrupt the LOV-HTH domain interactions and expose the HTH 4$\alpha$-helix. The HTH 4$\alpha$-helix then binds to another HTH on a second EL222 molecule generating an EL222 dimer that subsequently binds DNA. In addition, the LOV domain photochemistry is reversible, in one embodiment, spontaneously shutting itself off after about 30 seconds in the dark.

In another embodiment, the system of the invention can be tuned to have different kinetics of activation and/or inactivation using point mutations. For instance, the rate of spontaneous "shutting off" can be altered with point mutations, for instance, to residues near the chromophore binding site. Initial evaluation of several mutations as described in the Examples below (Table 4) shows that these changes can either accelerate this rate (e.g. Alanine 79 replaced by Arginine is accelerated ten-fold) or slow it (e.g. a variant combining changes at 41, 52, 79 and 121 exhibits 75-fold slower reversion). These variants can be used individually or in combination with others in the table or other variants. Such variants find use in many techniques as will be appreciated by those in the art. For instance, in certain embodiments, such variants may be useful for applications where transiently-induced gene expression is desired for studies of rhythmic biological phenomena.

In a further embodiment, the LOV domain may be activated or turned on again after a period of inactivation by further illumination with blue light. It is therefore possible to have multiple cycles of activation and inactivation through repeated cycles of blue light exposure and dark. In some embodiments, these pulses of light and dark may comprise equal periods of time in the light and time in the dark, or may comprise uneven periods, where the cells are exposed to light for a longer or shorter time than they are left in the dark. Such periods may comprise 5 seconds, 10 seconds, 20 seconds, 30 seconds, 40 seconds, 50 seconds, 60 seconds, 70 seconds, 75 seconds, 2 minutes, 3, minutes, 4 minutes, 5 minutes, 10 minutes, 15 minutes, 20 minutes, 25 minutes, 30 minutes, 1 hour, 2 hours, 3 hours, 4 hours, 5 hours, 6 hours, 7 hours, 8 hours, 9 hours, 10 hours, 12 hours, 20 hours, 22 hours, 24 hours, 36 hours or 48 hours. In other embodiments, the pulses may be repeated for multiple rounds of activation and inactivation, and such pulses may or may not comprise equal periods of time per round.

DNA-binding domains, in general, are well known in the art, and refer herein to protein domains that recognize a specific or consensus DNA sequence. Alternatively, a DNA binding domain may have a general affinity to DNA, without recognizing a specific sequence. The motif or motifs within a DNA-binding domain that recognize DNA can recognize and bind to double- or single-stranded DNA. There are numerous DNA-binding domains known in the art, including helix-turn-helix domains, helix-loop-helix domains, zinc finger domains, leucine zipper domains, and high mobility group box domains. A DNA-binding domain of the present invention may comprise any DNA-binding domain known in the art.

In a particular embodiment, the light-responsive DNA-binding protein of the invention is operably linked to a heterologous regulatory or functional domain or protein. Such domains may comprise, for instance, general transcription factors, transcriptional activators, transcriptional enhancers and transcriptional repressors. In one embodiment, the light-responsive DNA-binding protein of the present invention is operably linked to a transcriptional activation domain. Such linkage can be through the form of a fusion protein. A fusion protein as referred to herein describes a protein operably linking or connecting two or more proteins such that each protein continues to serve its intended function. Such proteins are typically linked via peptide bonds and may be constructed using standard techniques known in the art. It is understood that one of skill in the art may combine multiple proteins to create fusion proteins and may also alter the proteins comprising the fusion protein by inserting, deleting or rearranging the amino acid sequence of the proteins or domains within the proteins to produce variants that retain the intended function. Also included herein are nucleic acids encoding a LRDP operably linked to a transcriptional activation domain.

The transcriptional activation domain may be selected from any transcriptional activation domain known in the art, including but not limited to, acidic transcriptional activation domains, such as from GAL4 or the C-terminal portion of the herpes simplex virus viron protein 16 (VP 16); proline-rich transcriptional activation domains, such as from CTF/NF 1 or AP2; serine or threonine-rich transcriptional activation domains, such as from ITF 1 or ITF2; or glutamine-rich transcriptional activation domains, such as from Oct1 or Sp1. Other suitable transcriptional activation domains are known in the art and would be readily available to one of skill in the art.

The present invention is broadly applicable to gene expression in any cell, including eukaryotic cells, such as mammalian, insect, plant, yeast and fungal cells; and pro-karyotic cells, such as bacterial cells. Cells encompassed by the present invention include individual cells, cell lines, cells in culture, cells to be modified for gene therapy purposes, cells modified to create transgenic or homologous recombinant organisms, cells comprised in part of an organism or cells comprised in an entire organism. Examples of such cells include CHO dhfr-cells, 293 cells, myeloma cells such as SP2 or NSO, hematopoeitic stem cells, myoblasts, hepatocytes, lymphocytes, neuronal cells, skin epithelial cells, airway epithelial cells, embryonic stem cells, fertilized oocytes, plant root cells, leaf cells, flower cells, and cells from seed. Accordingly, principles of the present invention include a cell comprising a nucleic acid encoding a LRDP and/or a LRDP polypeptide.

Nucleic acids according to the invention, such as those encoding the light-responsive DNA-binding domain protein or comprising DNA binding sites may be introduced into a host cell for the regulation of gene expression of such a cell in any manner known in the art, for instance, through transformation or transfection techniques known in the art. Techniques for transformation and transfection of animal, plant, fungal, insect and other cells are available to those of skill in the art and include, but are not limited to calcium phosphate co-precipitation, DEAE-dextran-mediated transfection, lipofection, electroporation, microinjection, polyethylene glycol-mediated transformation, viral infection, *Agrobacterium*-mediated transformation, cell fusion, and ballistic bombardment. Cells comprising the nucleic acids according to the invention may be transiently or stably transformed. Such cells may therefore transiently or stably express the gene product, such as the encoded light-responsive DNA binding domain of the present invention. Suitable methods for transforming host cells may be found in Sambrook, et al. (Molecular Cloning: A Laboratory Manual, 2nd Edition, Cold Spring Harbor Laboratory press (1989)) and other laboratory manuals.

Regulatory sequences to be operably linked to nucleic acids according to the invention for introduction into a host cell may include promoters, enhancers, leaders, introns, polyadenylation signals and other expression control elements. Regulatory sequences are known in the art and are available to those of skill in the art. (See, Goeddel, Gene Expression Technology: Methods in Enzymology 185, Academic Press, San Diego, Calif. (1990)). The design of a suitable expression vector may depend on various factors including the host cell to be transformed or transfected or the level of gene expression desired. Nucleic acid molecules according to the invention may therefore be introduced into a host cell via a recombinant expression vector comprising such nucleic acids. Alternatively, nucleic acids according to the invention can be operatively-linked to regulatory sequences, such as promoter, enhancer, leader or intron sequences, without additional vector sequences followed by introduction into a host cell.

The light-responsive DNA-binding protein regulates the expression of a gene of interest comprising or operably linked to DNA-binding sites recognized by the DNA-binding protein. The light-responsive DNA-binding protein and the target nucleic acid sequence should therefore both be present in the host cell or organism. The present invention therefore provides cells comprising a nucleic acid molecule encoding the light-responsive DNA-binding protein and/or a nucleic acid molecule comprising a DNA-binding site recognized by the DNA-binding protein operably linked to a transcribable polynucleotide sequence.

The target nucleic acid sequence may comprise an exogenous or heterologous transcribable polynucleotide operably linked to a DNA-binding site transformed or transfected into the host cell or organism in a manner similar to the introduction of the nucleic acid molecule encoding the light-responsive DNA-binding protein, as described above. In such a case, the nucleic acid molecules encoding the light-responsive DNA-binding protein and comprising the target transcribable polynucleotide sequence can be introduced into a host cell or organism linked as a single molecule or as two separate molecules, for instance by co-transformation or successive transformation of one molecule then the other.

Alternatively, the target nucleic acid molecule may be an endogenous transcribable polynucleotide sequence. In such a case, the DNA-binding site is incorporated into the host cell in such a manner that it is operably linked to the endogenous transcribable polynucleotide sequence. Operable linkage of the DNA-binding site to the endogenous transcribable polynucleotide sequence may occur through any method known in the art, for instance, by homologous recombination between the two sequences. Homologous recombination techniques and methods are well known and available to one of skill in the art.

In certain embodiments, the transcribable polynucleotide sequence comprised within the target sequence and that is operably linked to the EL222-binding consensus sequence may be any desirable transcribable polynucleotide sequence. For instance, a reporter sequence, a cell stress tolerance sequence, an industrial enzyme encoding sequence; a sequence encoding a biofuel production enzyme; a sequence encoding a cell lysis protein or a sequence encoding a cell regulatory protein. In particular, embodiments, reporter sequences of the invention may be any of the sequences known in the art that when expressed may be readily identified or measured. These sequences may be useful in identifying or selecting cells or individuals of interest and may include for instance green fluorescent protein (GFP) encoding sequences, luciferase encoding sequences, GUS genes, or lacZ genes. Cell stress tolerance sequence useful in the present application may provide tolerance to stresses including, but not limited to heat stress, drought stress, biotic stress, nutrient deficiency stress or oxidative stress. Many industrial enzyme encoding sequences are known in the art that may be useful in the present invention. These enzymes may include any enzyme that can provide a functional use in an industrial or commercial setting, such as amylase, protease, trypsin, pectinase, lipase, lactase, xylanase or catalase. One class of industrial enzyme may include biofuel production enzymes such as cellulase or ligninase. Cell lysis proteins are also well known in the art and include any enzyme or other protein that breaks down the structural integrity of a cell, such as lysozyme, proteinase K or lysin. There are numerous sequences known in the art encoding cell regulatory proteins that may be useful in the present invention, such as kinase regulatory proteins, regulators of cell metabolism, regulators of cell differentiation, or regulators of cell division or growth.

The target nucleic acid sequence, in one embodiment may encode a protein of interest for light-dependent control of the expression of such protein. Alternatively, the target nucleic acid sequence may be transcribed into an active RNA molecule, such as transfer or ribosomal RNA molecules, or into a RNA molecule for gene suppression in the cell, such as an antisense RNA, dsRNA, shRNA, siRNA or miRNA molecule. Transcription of such molecules under control of the system of the present invention may therefore provide light-dependent regulatory control within the host cell, for instance, via protein expression inhibition or suppression. In one embodiment, the system, methods, proteins and nucleic acids of present invention are therefore useful in any instance where it is desirable to control gene expression in a targeted, rapid and reversible manner without undesirable pleiotropic effects or cytotoxicity. In a certain embodiment, the invention may be useful, for instance, for developmental studies, in which gene expression is only desired or necessary during a particular stage of development; treatment of diseases via gene therapy, where localized expression is particularly desirable; removal or reduction of undesirable gene products in a conditional manner via antisense or ribozyme molecules, for instance to alter biochemical pathways; large scale production of a protein of interest when desired; production of transgenic plants or animals without expression of the target transcribable polynucleotide effecting proper development, or to target particular tissues within such transgenic organisms.

Expression of the target nucleic acid molecule is controlled via exposure to blue light, for instance light at wavelengths about 350 nm to about 500 nm, for instance, about 400 nm to about 450 nm.

Variants of the light-responsive DNA-binding protein are also provided by the present invention. Nucleic acid and protein variations can be made by one of skill in the art using conventional techniques well known in the art. In one embodiment, variants of the light-responsive DNA-binding protein alter the responsiveness and/or reversibility of the resulting gene expression. For instance, variants rendering the light-responsive DNA-binding protein more or less responsive to the blue light, or requiring more or less exposure to the light, or exposure for more or less time are encompassed by the present invention.

The invention also provides for methods for separation, isolation or detection of at least one desired target moiety, such as a nucleic acid molecule. Such methods comprise operably linking a DNA-binding site recognizing a light-responsive DNA-binding protein of the present invention to the target moiety, contacting the light-responsive DNA-binding protein of the present invention to the target moiety or sample comprising the target moiety in the presence of blue light and thus separating, isolating, or detecting the target moiety. Release and collection for analysis such as identification of the target moiety may be achieved by removing exposure to blue light. Alternatively, analysis, such as identification, may be performed while the target moiety is bound to the light-responsive DNA-binding protein. Detection moieties may also be used operably linked to the light-responsive DNA-binding protein. For instance light-responsive DNA-binding proteins bound in the presence of blue light to DNA-binding sites operably linked to a target moiety may be distributed on an array and detected via an operably linked detection moiety, such as a green florescent protein, green florescent protein variants, enzymatic label or other isotopic or optically detectable labels.

Kits containing any components needed for light-regulated gene expression are also provided in the present invention. In one embodiment, a kit according to the present invention comprises a kit for the separation, isolation or detection of at least one desired target moiety, such as a nucleic acid molecule. Such a kit may comprise nucleic acids of the invention, such as nucleic acids comprising the target DNA binding sequences or proteins according to the present invention, such as a light-responsive DNA-binding protein. A kit according to the invention may further optionally comprise a column, an array, a binding matrix or bead, a detection moiety, such as an isotopic or optically detectable label, and any necessary buffers or solutions for the purification or separation of the desired nucleic acid molecule.

In another embodiment, the present invention provides a kit useful for regulating expression a gene of interest in a target cell or organism. Such kits may include nucleic acids according to the invention, such as nucleic acids encoding a light-responsive DNA-binding protein or nucleic acid molecules comprising the target DNA binding sequences or both. Said nucleic acid molecules may be provided or comprised within one or more vectors, such as an expression vector, and such vector may optionally comprise further elements, such as an operatively-linked minimal promoter, enhancer, intron or other regulatory sequence, or a cloning site for the introduction of any genes of interest or genes targeted for expression controlled via the light-responsive DNA-binding system of the present invention.

Alternatively, a kit of the invention may comprise cells comprising nucleic acids according to the invention or cells in which nucleic acids according to the invention have been stably incorporated therein. Such nucleic acid molecules may comprise nucleic acids encoding a light-responsive DNA-binding protein or nucleic acid molecules comprising the target DNA binding sequences or both. In one embodiment, a kit of the invention comprises cells expressing a light-responsive DNA-binding protein of the invention. The present invention further provides methods of using a kit of the invention.

In yet another embodiment, the present invention provides methods for selectively recruit proteins to a surface, such as the surface of a substrate, for instance in a light-dependent manner. Such methods may in one embodiment be employed for use in a microarray system. Microarray systems, such as those from Illumina or Affymetrix are well known in the art. In certain embodiments, such methods may comprise immobilizing to or coating a surface with DNA-binding sequence molecules, exposing the surface to a light-responsive DNA-binding protein of the invention and selectively illuminating said surface. By DNA-binding sequence molecules is meant nucleic acids having a sequence to which the DNA binding domain of an LRDP binds. Upon illumination, the light-responsive DNA-binding protein may become associated with DNA-binding sequence molecules on the surface of the substrate, thus recruiting these proteins and any binding partner, such as a nucleic acid or protein, in association with or linked to the light-responsive DNA-binding protein. Thus, in one embodiment, the light-responsive DNA-binding protein may be associated with or linked to, for instance through a fusion protein, any protein of interest. In another embodiment, a light-responsive DNA-binding protein of the invention may be recruited to a surface using such methods in a spatial pattern through selective spatial illumination of the surface. In some embodiments nucleic acids immobilized on the substrate surface have different sequences and are distributed at discrete sites on the substrate surface.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Engineering the EL222 Protein

Figure 1B:
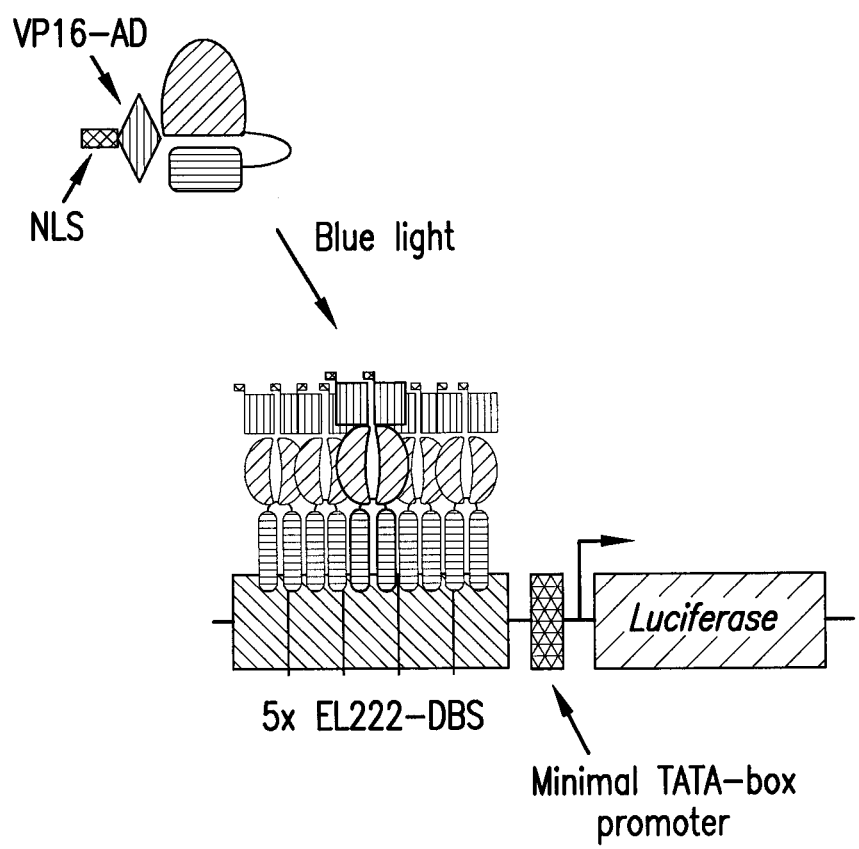

The first step taken to adapt the EL222 prokaryotic transcription factor for use in eukaryotic cells (FIG. 1) was to modify EL222 with nuclear localization and activation domains (not present in the natural protein), without hindering DNA binding or light regulation. The transcriptional activation domain (AD) from the herpes simplex virus VP16 protein, which is routinely used to efficiently recruit components of the mammalian transcription machinery to a target gene (Blau et al., Mol Cell Biol (1996)16: 2044), was fused to the EL222 coding sequence (FIG. 1b). A nuclear localization signal (NLS) was also added to properly localize the VP16-EL222 fusion protein to the nucleus. Expression of the VP16-EL222 chimera is driven from the constitutively active SV40 early promoter.

Methods

A. Vector Construction

DNA encoding a 13-residue N-terminal truncation of WT-EL222 (residues 14-222), provided as SEQ ID NO:72, was cloned into the expression vector pHis$_6$-Gβ1-Parallel1 (Nash et al., PNAS 108 (2011): 9449).

The rate-altering A79Q-EL222 variant, provided as SEQ ID NO:76, was produced using the QUIKCHANGE protocol (Stratagene) within the context of the N-terminally truncated EL222 (Zoltowski et al., Biochemistry (2011): 8771). The A79Q-EL222 variant was subcloned into a pHis$_6$-Parallel1 expression vector.

B. Purification of EL222 Protein

WT-EL222 and A79Q-EL222 proteins were expressed in E. coli BL21 (DE3) cells. Cells were grown in LB-AMP at 37° C. in the dark and were induced with 0.5 mM IPTG. After a 20 hour induction at 18° C., cells were centrifuged and resulting pellets resuspended in buffer A (50 mM Tris-Cl pH 8.0 and 100 mM NaCl) and subsequently lysed by sonication. The protein was purified in the dark at 4° C. by gravity-flow chromatography with Ni-NTA agarose (Qiagen) equilibrated in buffer A. Proteins were eluted in buffer B (50 mM Tris-Cl pH 8.0, 100 mM NaCl, 75 mM imidazole), exchanged into buffer A and concentrated to 100-200 µM.

Example 2

Identification of High Affinity DNA Binding Sites

In addition to modifying the EL222 protein, a high-affinity cognate DNA binding site (EL222) was identified and used to construct a reporter vector with tandem copies of this and a minimal TATA-box promoter in front of a Firefly luciferase gene as a test transgene. Several sites were initially identified for this purpose using a candidate-based approach based an in vitro DNA binding assay (EMSA, Electro Mobility Shift Assay) of approximately 15 sequences located upstream of the EL222 gene itself (Nash et al., 2011). From these candidates, one DNA site was identified (AN-45) that bound EL222 best in the group with an EC$_{50}$ of 5-10 µM. Importantly, DNA binding occurred only when the protein/DNA mixture was exposed to light and not when kept in the dark, as expected from the presence of the photosensitive LOV domain. However, while the AN-45 substrate bound with the highest affinity of this limited set of oligonucleotides, it was suspected that this was not an optimal binding site given DNA-binding affinities for other HTH-containing proteins (Zhu and Winans, Proc. Natl. Acad. Sci. 98 (2001): 1507) and it did not prove to be useful in pilot studies of this light-activated gene system.

Figure 2A:
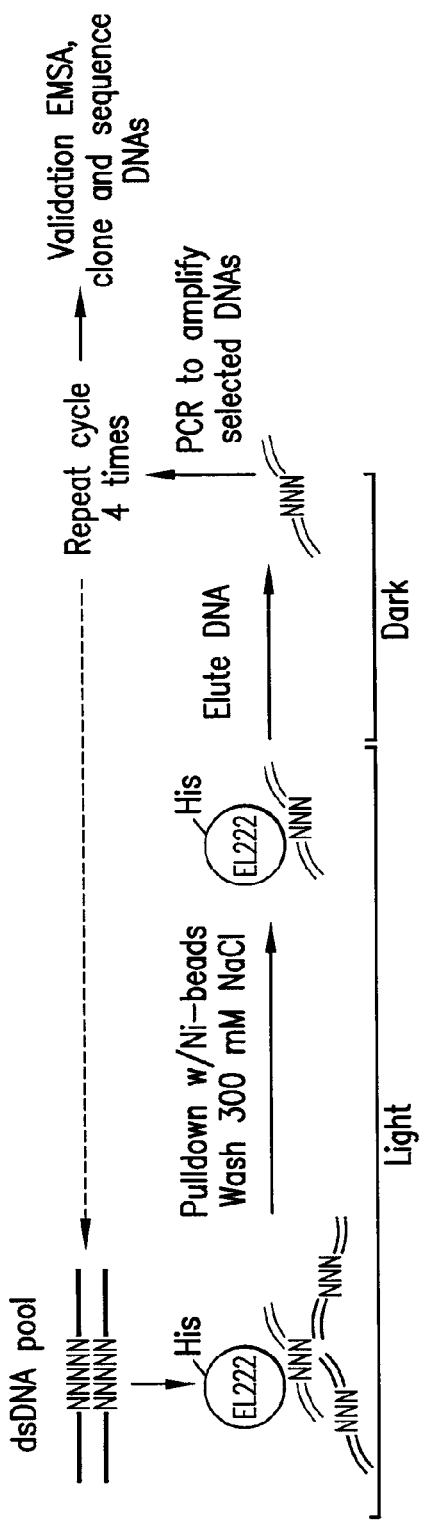
FIG. 2. Demonstrates the use of an in vitro oligonucleotide-protein binding selection assay (SELEX) (Tuerk and Gold, *Science* 249 (1990): 505) to identify high-affinity EL222 target sequences. Panel "a" shows a schematic of the SELEX enrichment protocol to identify EL222 binding sites. Panel "b" shows EMSA results of EL222 binding to $^{32}$P-labeled DNA pools derived from SELEX (or the previously identified EL222 substrate AN-45; Nash et al., 2011); mixtures were exposed to light for 25 min before loading and electrophoresing on a native PAGE gel.

To identify additional DNA sequences with higher affinity for EL222, an in vitro selection method was used (SELEX, Systematic Evolution of Ligands by EXponential enrichment; Tuerk and Gold, Science 249 (1990): 505). For this assay a large double-stranded oligonucleotide library (~5× 10$^{14}$ molecules) was synthesized consisting of randomly generated 33 bp sequences flanked by constant 5' and 3' ends (each 21 bp long) with primer binding sites (FIG. 2a). The oligonucleotide library was next incubated with recombinant His$_6$-tagged EL222 protein in a 2:1 (DNA:protein) ratio and the mixture was exposed to light to activate the protein. The EL222/DNA complexes were purified by affinity chromatography using Ni-NTA beads under stringent binding conditions. Next, the purified EL222/DNA complexes were incubated in the dark to inactivate the protein and elute the DNAs. The DNA sequences were amplified by PCR and then used to set up a second round of selection; the entire cycle was repeated a total of four times. Gel mobility shift assays were done after each selection cycle to verify that the binding affinity of the DNA pools increased after each successive round (FIG. 2b, Rounds 1-4).

Figure 2B:
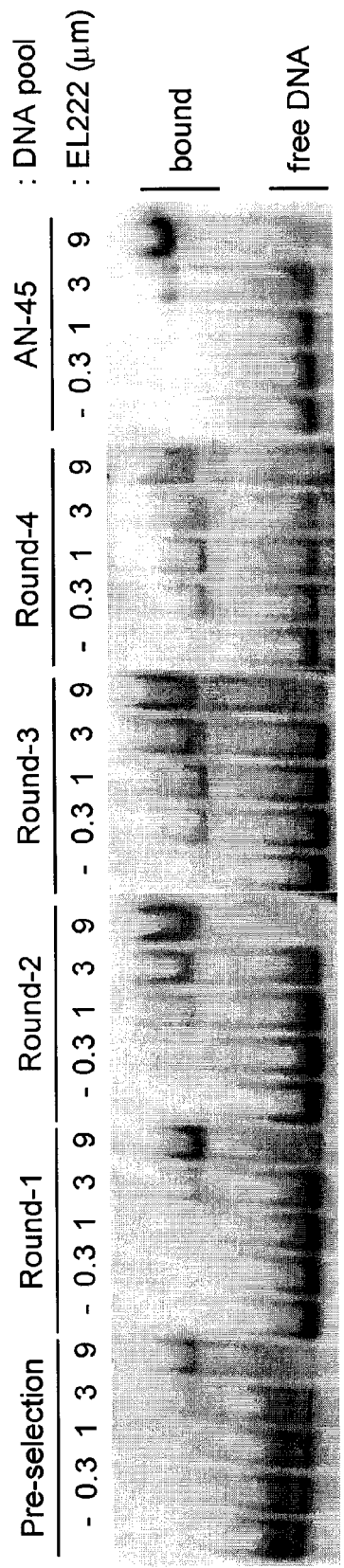
Figures 3A, 3B:
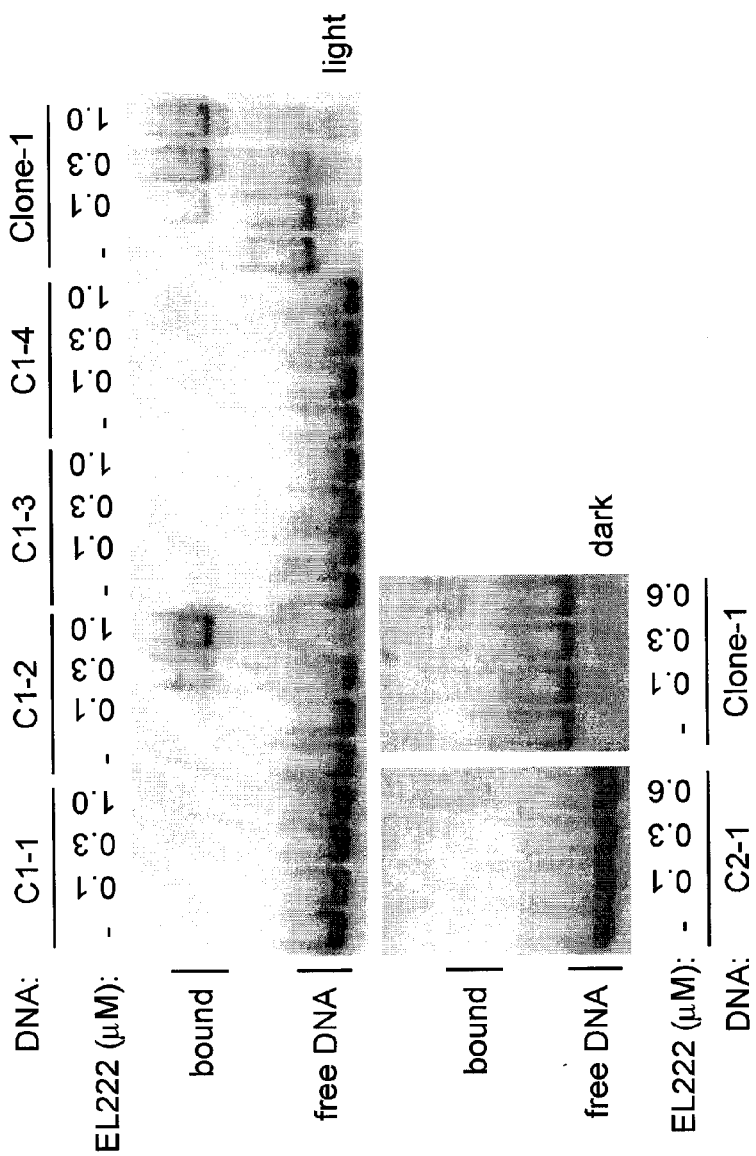
FIG. 3. Demonstrates mapping of the EL222 binding site within the SELEX-derived Clone-1 DNA. Panel "a" shows a schematic of the scanning analysis of Clone-1 (SEQ ID NO:68), which contains the 33-bp randomized region (upper case) flanked by 6 bp of primer binding sequence (lower case). The locations of each 20 bp Clone-1-derived DNAs (SEQ ID NOs:63-66) are given for each fragment. Panel "b" shows EMSA of EL222 binding to each DNA, using the same conditions as FIG. 2.

As predicted, by the fourth round of SELEX a pool enriched with DNAs with higher affinity for EL222 than the AN-45 substrate was obtained (FIG. 2b, Round 4 as compared to pre-selection). DNAs from SELEX round 4 were further cloned and sequenced. A total of 60 DNA sequences were cloned, but because some of these sequences were repeated, only 57 unique DNA sequences were obtained. A complete list of these sequences is shown in Table 1 and Table 2. Based on analyses using the motif-based sequence analysis tool MEME, seven DNA sequences were chosen for follow-up binding studies (Table 1). EMSA assays showed that Clone-1 bound with the highest affinity to EL222 out of the seven DNAs tested, with a 30-50 fold higher affinity than AN-45 (EC$_{50}$ value of 100-300 nM; Table 1, FIG. 2b). To further delineate the sequence within 45-bp Clone-1 DNA most relevant to EL222 binding, 4 overlapping 20-bp fragments derived from Clone-1 were designed and their binding to EL222 was assessed by gel mobility shift assay (FIG. 3). Interestingly, only the C1-2 fragment, which contains the full motif identified by MEME (see Table 1), was bound by EL222, while fragments C1-1 and C1-3 do not bind EL222 despite containing halves of the motif.

TABLE 1

Seven DNA sequences chosen for follow up and their half maximal effective concentration (EC$_{50}$) values for binding to EL222. The identified 14 bp consensus motif is shown in bold.

| Name | DNA sequence (33 bp randomized region) | SEQ ID NO: | EC$_{50}$ (µM) |
|---|---|---|---|
| Clone-1 | TTATAGGTAGCCTTTAGTCCATGCTGATTCGTT | 4 | 0.1 < EC$_{50}$ < 0.3 µM |
| Clone-3 | TAGACTTAAGTCTAGTACACAAGTTTTCCAGGG | 5 | 0.3 < EC$_{50}$ < 1 µM |
| Clone-2 | AGCTAGGCTTTTGGTCTGTATAGCTGTCTTATA | 6 | 0.5 < EC$_{50}$ < 1 µM |
| Clone-22 | TATAGGGCTTTAGTCTGTATGTGGGATGTGTGT | 7 | 0.5 < EC$_{50}$ < 1 µM |

TABLE 1-continued

Seven DNA sequences chosen for follow up and their half maximal effective concentration (EC$_{50}$) values for binding to EL222. The identified 14 bp consensus motif is shown in bold.

| Name | DNA sequence (33 bp randomized region) | SEQ ID NO: | EC$_{50}$ (μM) |
|---|---|---|---|
| Clone-53 | CATGGCCTAAGGACTGTAAGTACTATTAAATAC | 8 | 0.5 < EC$_{50}$ < 1 μM |
| Clone-77 | CAGATACATGCTTTAGTACGTATATTCGATGTC | 9 | 0.5 < EC$_{50}$ < 1 μM |
| Clone-78 | GCCCTAAGACTGTATCTTATTCGTGAGTTTTAA | 10 | 0.5 < EC$_{50}$ < 1 μM |
| Consensus motif: G[C/G]CTT[T/A][A/G]G[T/A]C[T/C]GTA | | 67 | |

TABLE 2

List of 50 additional DNA sequences derived from SELEX.

| Name | DNA sequence | EC$_{50}$ (μM) | SEQ ID NO: |
|---|---|---|---|
| Clone-4 | AAATCGAGGGGCCGAGGTCTCCTTTCCTTGACA | n.d. | 11 |
| Clone-5 | ACCTTACAAAGCTAATAATTCTTCCTTCAAACG | n.d. | 12 |
| Clone-6 | TGTTCAGGGGTATGCCTACGCTGGATCAGCCGT | n.d. | 13 |
| Clone-9 | GTGACCGTTCCGTATTCATTATTCACACATAAT | n.d. | 14 |
| Clone-10 | TCGCATTAGAATGGCTGGGACGGTTAGTGTTGG | n.d. | 15 |
| Clone-15 | TTAGGCACTTGTGACTTGACGTTGTTTGTACAT | n.d. | 16 |
| Clone-16 | TTCTGAGGAAGATGAAGATGACAGGCATGTGTA | n.d. | 17 |
| Clone-17 | CAGTCTTTCTCTCTCGTCGACGATGTATTTTCT | n.d. | 18 |
| Clone-18 | ATTTTTGGTGGGAGTATTAGTACGAACGGCTGT | n.d. | 19 |
| Clone-29 | TTCAATCGCTAGCTACCTTACTCGTTAATAAAG | n.d. | 20 |
| Clone-38 | GACCAAAGTGCAATGGTCCAATTCGGTTATGCC | n.d. | 21 |
| Clone-39 | GTATTTAATTGCAGAGAAAATCTTTATCTTCTT | n.d. | 22 |
| Clone-40 | GTTCGCTTTGAATGTAACGGACTCGTGAGATTT | n.d. | 23 |
| Clone-41 | CATTCAAAAGTACGCGAGGTTTTGGTGCTACTT | n.d. | 24 |
| Clone-42 | GTCTAAGGACTAGGTGTGTTCCTCTGGATCTCG | n.d. | 25 |
| Clone-43 | AGGGTCGCTCAGCATAAAGGTTGCAATTACGGT | n.d. | 26 |
| Clone-44 | AAAGTCTAGTATTGTACACCTCCTCTCGGTAAA | n.d. | 27 |
| Clone-45 | ATCAGGGACATAGAACGCTAAGACTCGCCTGCA | n.d. | 28 |
| Clone-46 | GGTGCCGGTGAGTACCATGGACCTTGGTAACTT | n.d. | 29 |
| Clone-47 | AAGTGACGATTACATACCCCGTATACCGTATCA | n.d. | 30 |
| Clone-48 | CTGATACTATAGCTACCTTTGATGGTTTTCATA | n.d. | 31 |
| Clone-49 | GTCTTTTGGGCATGTTGTGAATAAGAAGCCAAA | n.d. | 32 |
| Clone-50 | ACAAAAGCCTGTGCGGTAAGAAATGAGTTTTAA | n.d. | 33 |
| Clone-54 | ACCCAGTCGACTTCAAGGATATAATAAACCCGT | n.d. | 34 |
| Clone-55 | TACTTAAGGACTATATAAGGGTTTACTGATCGT | n.d. | 35 |
| Clone-56 | TTGGTACATTATACAAGCGTGAGAGGACTGGCT | n.d. | 36 |
| Clone-57 | TCGAAAAGCTACGGTCATTATGTAGGACTGTCG | n.d. | 37 |
| Clone-61 | TACGTTGGGTGTTTTTAATCCCGGAAATGCGT | n.d. | 38 |
| Clone-62 | CAGTCTTTATCTCTCGTCGACGATGTATTTTCT | n.d. | 39 |
| Clone-63 | CGTCGATGAGAACCTCGGAGACATGGCCAGTCT | n.d. | 40 |
| Clone-64 | CTATGTATCTACGTGAATGGATACGGTCTTTTT | n.d. | 41 |
| Clone-65 | TATTAAGCCTAGGGGTCCTATTACCCTTAGACT | n.d. | 42 |
| Clone-66 | CTATAGGTGACTGCGGGTATGAGAGTAGTGGGA | n.d. | 43 |
| Clone-67 | TAGCCCATTTATTGTTTGAAAGCGCATTTGTCA | n.d. | 44 |
| Clone-68 | GTTATGTTTGGCGACGCGCCGGTTAGTCTCCTT | n.d. | 45 |
| Clone-71 | GCCTTTATGCTTATACGTGCCGATTTCCCAAAT | n.d. | 46 |
| Clone-74 | TTATTAAGTCCGTATTAAGTATGGAGGGAGAGG | n.d. | 47 |
| Clone-76 | GCACAATGTCCACCCTCACGCCATACTTATTGA | n.d. | 48 |
| Clone-79 | GTTCCTTGGGATGAGCTCGTATGCACATGGTAT | n.d. | 49 |
| Clone-81 | GGTTGAATAGTTATAATGCGACCTGGACTCTTT | n.d. | 50 |
| Clone-82 | CAAACGTCATGGTCAACGTATTTACACTAGATC | n.d. | 51 |
| Clone-83 | TGTTGAGTTCATAGGAAGGGCTGTAGACATTC | n.d. | 52 |
| Clone-84 | CCATTTGAGATGTATAGCGGACCAGAAATGGTT | n.d. | 53 |
| Clone-85 | CGATTGACTGTATGGACCTTAATATAGTTTGTA | n.d. | 54 |
| Clone-86 | TACTATAGGATTGTTAGCCCTGAAGAGCAGGTG | n.d. | 55 |
| Clone-87 | CAGTGCGCTAGCTAATACTCCCTTGTTTTACCT | n.d. | 56 |
| Clone-88 | ACCTTATGACCAGGTTGTTGGACTGATTGTAAC | n.d. | 57 |
| Clone-89 | TCCTTCAGTCTCTACTTATTAAAGGCTTGAAAG | n.d. | 58 |
| Clone-90 | TCAGGGACATTGGGCTACGATTATCTACCTTA | n.d. | 59 |
| Clone-91 | GTCGTTAGGAGGTACTTTGAACGCCACCATCAT | n.d. | 60 |
| Clone-92 | CCTGCTTGGCAAGATCTTACCGGGGTTTGGTAG | n.d. | 61 |
| Clone-93 | GTATTTAAGCCATACTATTGTCTTAGCCGCGAG | n.d. | 62 | n.d. - not determined.

TABLE 3

List of the DNA sequences derived from Clone-1, used to map regions of specific binding (FIG. 3). Each sequence is 20 bp long.

| Name | DNA sequence | $EC_{50}$ (μM) | SEQ ID NO. |
|---|---|---|---|
| C1-1 | TCTACGTTATAGGTAGCCTT | n.d. | 63 |
| C1-2 | TAGGTAGCCTTTAGTCCATG | 0.3 < $EC_{50}$ < 0.5 μM | 64 |
| C1-3 | TTTAGTCCATGCTGATTCGT | n.d. | 65 |
| C1-4 | TGCTGATTCGTTTTCAACTT | n.d. | 66 | n.d. - not determined.

TABLE 4

Rate-altering variants of EL222 and their effect on EL222 kinetics.

| EL222 Variant | Lit state lifetime @ 25° C. | SEQ ID NO: |
|---|---|---|
| wildtype | 25 s | 73 |
| V41I | >25 s | 74 |
| L52I | >25 s | 75 |
| A79Q | 300 s | 76 |
| A79R | 2.5 s | 77 |
| A79T | 8 s | 78 |
| V121I | >25 s | 79 |
| V41I:L52I | >25 s | 80 |
| V41I:A79Q | >25 s | 81 |
| V41I:V121I | 300 s | 82 |
| L52I:A79Q | >25 s | 83 |
| V41I:L52I:V121I | 1800 s | 84 |
| V41I:L52I:A79Q:V121I | 1800 s | 85 |

Lit state lifetimes were measured by visible absorbance spectroscopy after excitation. Values designated ">25 s" are approximate.

Methods

A. SELEX Procedure

The initial single-stranded oligonucleotide 5'-GGGAATGGATCCACATCTACG-(N)$_{33}$-TTCAACTT-GACGAAGCTTGCC-3' (SEQ ID NO:1) was chemically synthesized by Integrated DNA Technologies (IDT). To amplify the DNA pool, six 50 μl PCR reactions were set up using (final concentrations): 0.1 μM of the synthetic pool oligonucleotide as template, 2 μM primers, 200 μM dNTPs, 20 mM Tris-Cl pH 8.8, 10 mM $(NH_4)_2SO_4$, 10 mM KCl, 2 mM $MgSO_4$, 0.1% Triton X-100, 4 mM $MgCl_2$, and 0.04 U Vent (New England Biolabs Inc.). The primers used were Fwd-L1 5'-GGGAATGGATCCACATCTACG-3' (SEQ ID NO:2) and Rev-L1 5'-GGCAAGCTTCGTCAAGTTGAA-3'(SEQ ID NO:3). The cycling parameters were as follows:

Initial denaturation: 94° C. 2 min
11 cycles: 94° C. 45 sec
60° C. 45 sec
72° C. 45 sec
Final extension: 72° C. 5 min Amplified DNAs were purified using QIAQUICK PCR purification kit (Qiagen). Approximately 15.7 μM DNA ($5 \times 10^{14}$ molecules) and 7.8 μM A79Q-EL222 protein were incubated in a total volume of 500 μl containing (final concentrations): 10 mM Tris-Cl pH 8.0, 80 mM NaCl, 3 mM $MgCl_2$, 10% glycerol, 0.025 mg/mL polydI-dC, and 0.01 mg/mL BSA. The binding reaction was mixed by rotation for 25 min at 4° C. and kept under continuous illumination with a white LED light. Ni-NTA agarose beads (Qiagen) were pre-blocked with 0.02 mg/mL of polydI-dC and then added to the binding reaction and incubated for an additional 25 min at 4° C. with mixing and continuous illumination. The bead/EL222/DNA complexes were pulled down by centrifugation at 2000 rpm for 1 min at 4° C. Next, complexes were washed with 300 μl of buffer C (50 mM Tris-Cl pH 8.0, 300 mM NaCl) and pulled by centrifugation, this step was repeated at least 2 more times. After the last wash, the bead/EL222/DNA complexes were resuspended in 400 μl of binding buffer (without polydI-dC and BSA) and incubated in the dark for 30 min at 4° C. with mixing by rotation. The beads/EL222 complexes were pulled down by centrifugation and the supernatant (containing the DNAs) was transferred to a new Eppendorf tube.

Phenol/chloroform/isoamyl alcohol was added to the supernantant in a 1:1 ratio, the sample was vortexed and centrifuged at 13,000 rpm for 5 min at 4° C. The top aqueous phase, which contains the eluted DNA, was transferred to a new Eppendorf tube containing 1 ml of 100% ethanol, 0.3 M NaOAc pH 5.2, and 0.01 mg/mL glycogen. The DNA was precipitated overnight at –20° C. and subsequently recovered by centrifugation at 13,000 rpm for 20 min at 4° C. The pelleted DNA was resuspended in 12 μl of DNase-free water and later used as the template DNA pool in a second PCR amplification step and round of selection. To sequence individual DNA sequences from the DNA pools obtained after each SELEX round, the DNA pools were cloned into the pBlueSkript+ vector using BamHI and HindIII restriction sites.

B. Electrophoretic Mobility Shift Assay

DNA pools derived from each SELEX cycle were PCR amplified as described previously in the SELEX procedure. Complementary oligonucleotides for each individual SELEX-derived clone sequence were chemically synthesized (Sigma), heated to 95-100° C. for 5 min and left to cool to room temperature to anneal the oligonucleotides. DNAs were 5'-end labeled in a 50 μl reaction containing (final concentrations) 68 nM DNA substrate, 70 mM Tris-Cl pH 7.6, 10 mM $MgCl_2$, 5 mM DTT, 0.6 μCi ATP [γ-$^{32}$P] (Perkin Elmer, cat. no. BLU502Z500UC), and 0.2 U PNK (New England Biolabs Inc.). The reaction was incubated for 30 min at 37° C., followed by a 20 min incubation at 65° C. to heat inactivate the enzyme. The $^{32}$P-labeled DNA was purified from the unincorporated ATP [γ-$^{32}$P] using Illustra ProbeQuant G-50 micro-columns (GE Healthcare). Approximately 13.6 nM radiolabeled DNA was incubated with varying concentrations of WT-EL222 in the same binding buffer used for SELEX procedure for 25 min at 4° C. with continuous illumination with a white LED light. Reactions were analyzed on a 5% native gel (Acrylamide/Bis 29:1) and run in TBE buffer at 150 V for 1.5 hr at 4° C. The gel was exposed to a PhosphorImaging plate and visualized using FujiFilm FLA-5100 imaging system.

Example 3

Light-Dependent Gene Activation in Eukaryotic Cells

Based on the in vitro binding data in Example 2, two reporter constructs were designed to test in cultured mammalian cells together with the VP16-EL222 fusion protein. Both constructs contained the Firefly luciferase gene under the control of five tandem copies of either the Clone-1 45-bp sequence or the C1-2 20-bp sequence (FIG. 4a). When co-transfected into 293T cells, the VP16-EL222 expression construct was able to activate transcription of the pClone1-45[Luc] and pClone1-20[Luc] reporters by 57-fold and 87-fold over empty vector controls respectively, when the cells were exposed to blue light (FIG. 4b). In contrast, dark state controls only showed about a 1.5 to 2-fold change in luciferase induction over empty vector for both reporters. After correcting for this small background induction in the dark, we calculated that for pClone 1-45[Luc] and pClone1-20[Luc] there is 25-fold and 58-fold increase in transgene expression dark-to-light, respectively. With changes to the illumination protocol to optimize conditions given the lifetime of the wildtype EL222 photoexcited state, we observed even higher fold activation (e.g. 108-fold activation, FIG. 5). Additional control experiments have shown that the activation of VP16-EL222 in mammalian cells is specific to blue light, as illumination with red light does not turn on transcription of Luciferase reporter (FIG. 7a). The specificity of the VP16-EL222 protein for the 20 bp C2-1 sequence (SEQ ID NO: 69) when transfected into mammalian cells was verified by experiments wherein reporter vectors under the control of nonspecific DNAs sequences were shown to not be turned on by EL222 either in the dark or with light (FIG. 7b). Taken together, this data demonstrate that the EL222 can function as a blue-light-regulated transcription factor that can be used to control transgene expression in mammalian cells.

Methods

A. Mammalian Vector Construction

For expression in mammalian cells, DNA containing the 13-residue N-terminal truncation (residues 14-222) of WT-EL222 was subcloned into the mammalian expression vector pVP16 (Clontech; catalog no. 630305) using EcoRI and XbaI restriction sites to obtain pVP16-EL222. The VP16-NLS-EL222 coding sequence is provided as SEQ ID NO:70. The corresponding amino acid sequence is provided as SEQ ID NO:71. The nuclear localization signal (NLS) corresponds to nucleotides 7-27 of SEQ ID NO:70 and amino acids 3-9 of SEQ ID NO:71. The VP16 activation domain corresponds to nucleotides 28-261 of SEQ ID NO:70 and amino acids 10-87 of SEQ ID NO:71. The EL222 ORF (14-222 aa) sequence corresponds to nucleotides 268-879 of SEQ ID NO:70 and amino acids 90-298 of SEQ ID NO:71 (FIG. 6). The NLS and VP16 regions were derived from the pVP16 Clontech vector. The rate-altering variants L52I-EL222 (SEQ ID NO:75), A79Q-EL222 (SEQ ID NO:76), and L52I/A9Q-EL2222 (SEQ ID NO:83) were subcloned into the pVP16 vector from Clontech (see FIG. 10).

The five tandem copies of the Clone-1 sequence (both the 20 bp and 45 bp version as shown in FIG. 4) were chemically synthesized by GeneArt (Invitrogen) and inserted into the pGL4.23 [luc/minP] construct (Promega) using XhoI and HindIII restriction sites to obtain pClone1-20[Firefly Luc] or pClone1-45[Firefly Luc]. To make the mCherry reporter construct the Firefly Luciferase coding sequence in pClone1-20[Firefly Luc] was replaced by the mCherry coding sequence using NcoI and XbaI. The resulting vector was named pClone1-20[mCherry]. Additional vectors were made that served as controls in experiments, these were the p3XAN45[Firefly Luc] and p5XUAS$_G$[Firefly Luc] constructs. The p3XAN45[Firefly Luc] vector was made by inserting three tandem copies of the AN45 DNA sequence (Nash et al., PNAS 108 (2011): 9449), which were chemically synthesized by GeneArt (Invitrogen), into the pGL4.23 [luc/minP] construct (Promega) using XhoI and HindIII. Similarly, for the p5XUAS$_G$[Firefly Luc] vector five tandem copies of the GAL4 upstream activation sequence (UAS$_G$) were amplified from the pG5SEAP vector (Clontech; catalog no. 630305) and subcloned into the pGL4.23[luc/minP] using XhoI and HindIII.

B. Light-Activation of Luciferase Transcription i. Constant Illumination

Human embryonic kidney cells (HEK-293T cells; ATCC) were cultured in DMEM (Thermo Scientific; cat. no. SH30284.01) supplemented with 10% fetal calf serum (FCS) and 1% penicillin/streptomycin (Pen/Strep) solution at 37° C. in 5% $CO_2$. Cells were co-transfected using LIPOFECTAMINE 2000 (Invitrogen) in an optimized protocol. On the day of transfection, a total of 495 ng of DNA (410 ng of pVP16(empty) or pVP16-EL222 DNA, 82 ng of pClone1-20[Firefly Luc] or pClone1-45[Firefly Luc] DNA, and 3 ng of pGL4.75 [hRluc/CMV] (Promega)) were diluted in 50 μl of Opti-MEM I Medium (Invitrogen; cat. No. 11058) and aliquoted into a 24-well plate. For each well, 1.25 μl of LIPOFECTAMINE 2000 was diluted in 50 μl of Opti-MEM I Medium and incubated for 5 min at room temperature. The diluted LIPOFECTAMINE 2000 was then added to each well containing the diluted DNA and incubated at room temperature for 20-30 min. During this incubation step the cells were trypsinized, washed with 10 mL of phosphate buffered saline solution and centrifuged at 1000 rpm for 5 min at room temperature. The cells were then resuspended in Pen/Strep-free DMEM+10% FCS and diluted to $1\times10^5$ cells per 500 μl. After the 30 min incubation step, 500 μl of the cell suspension were added to each of the wells containing the diluted DNA/ LIPOFECTAMINE 2000 mixture. At 24 hr after transfection, a blue LED array (LED wholesalers; 2501BU blue 225 LED 13.8 Watt square panel, 110 V) was placed above the 'light-treated' plate inside the cell incubator for an entire 24 hr period. The non-treated plate was kept in the dark throughout the experiment. At 48 hr after transfection, Luciferase activity was measured with the Dual-Glo Luciferase Assay system according to the manufacturer's instructions (Promega). A single experiment included identical transfections set up in triplicate for each condition (i.e., pVP16 (empty) and pVP16-EL222). The Firefly Luciferase data was normalized relative to Renilla Luciferase to correct for differences in transfection efficiency between samples. For this, the average of the triplicate Firefly Luciferase values are divided by the average of the triplicate Renilla Luciferase values for each condition. Next a ratio of ratio is calculated to obtain the fold change (FC) in activation, FC =[(Firefly/Renilla)$_{vp16-EL222}$/ (Firefly Renilla)$_{empty\ vector}$]. To calculate the fold change upon blue-light illumination, the FC$_{Light}$ for pVP16-EL222 was divided by the FC$_{Dark}$ for pVP16-EL222.

ii. Optimized Illumination Based on the Lifetime of EL222 Photoexcited State

A Firefly luciferase reporter construct under the control of 5 copies of 20-bp C1-2 (SEQ ID NO:69) sequence was co-transfected with the VP16-EL222 expression construct or a VP16 (empty) vector into HEK293T cells in a manner similar to that above. At 24 hr after transfection, the cells were kept in the dark or illuminated with blue light in an alternative fashion for 24 hours using an illumination schedule of (20 seconds light:60 seconds dark) through the 24 hour period. Afterwards, cells were harvested and luciferase activity was measured (left graph). Luciferase values were normalized for transfection variability using a control Renilla luciferase reporter with a constitutively active CMV promoter and was co-transfected with the Firefly luciferase reporter and VP16-EL222 expression vector. Results are provided in FIG. 5. A 108-fold enhancement in gene expression was observed with this illumination protocol, compared to 58-fold change observed with the same enhancer and constant illumination (FIG. 4b).

iii. Stable Cell Line that Expresses VP16-EL222 Protein

DNA containing the VP16 activation domain, the NLS, and the 13-residue N-terminal truncation (residues 14-222) of WT-EL222 was PCR amplified from the pVP16-NLS-EL222 vector and subcloned into the mammalian expression vector pIRESpuro (Clontech; catalog no. 6031-1), which contains a Puromycin resistance gene, using EcoRV and BamHI. The construct was named pIRESpuro-VP16-EL222. HEK293T cells were transfected with the pIRE-Spuro-VP16-EL222 and at 24-hr after transfection the cells were cultured in media containing puromycin at 2 µg/ml to select for those cells carrying the pIRESpuro-VP16-EL222 vector. Puromycin-resistant colonies were validated for expression of VP16-EL222 protein by western blotting with an anti-VP16 antibody (Abcam; catalog no. ab4808) (see section "vi" below). Of the colonies screened, the VP16-EL222 stable cell line named Clone-3 showed the highest level of protein expression and was therefore chosen for use in subsequent experiments.

The protocol for Luciferase transcription assays in the VP16-EL222 stable cell line was as follows. Clone-3 cells were transfected with the Firefly luciferase reporter construct under the control of 5 copies of 20-bp C1-2 sequence (SEQ ID NO:69) only. Immediately after transfection the cells illuminated with blue light in an alternative fashion for 3, 6, 9, 12 or 24 hours using an illumination schedule of (20 seconds light:60 seconds dark) or kept in the dark for the duration of the experiment. After each time point the cells were harvested and luciferase activity was measured. Results are provided in FIG. 11. Luciferase intensity was measured at over 1.3 million relative light units (RLU) in Clone-3 cells after 12 hr of illumination. Compared to the Luciferase intensity values we obtained when HEK293T cells were transiently transfected with VP16-EL222 and the p5XClone1-20[Firefly Luc] reporter vectors (~50-60,0000 RLUs), we observed over 20-fold higher light-driven activation of Luciferase transcription with the Clone-3 cell line that stably expresses VP16-EL222 (compare FIG. 5 (left panel) and FIG. 11a).

Figure 11A:
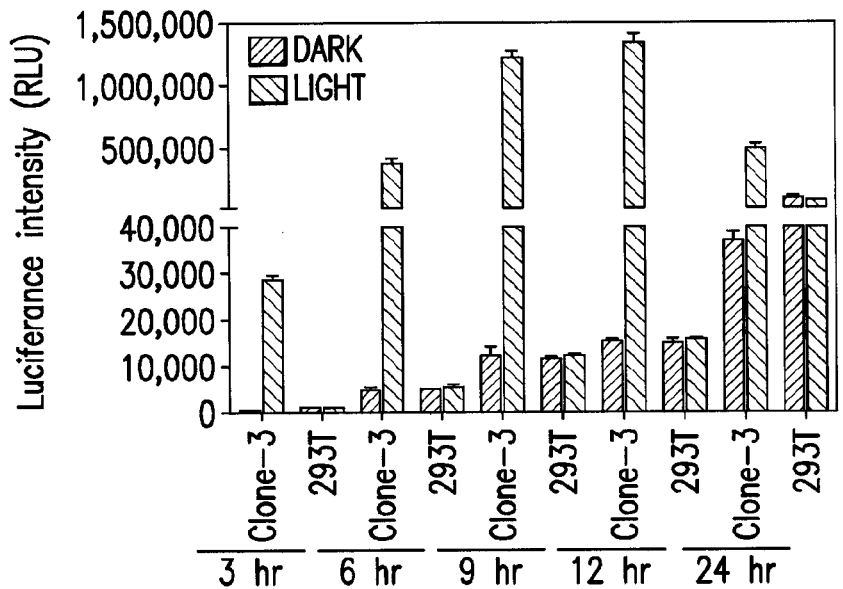
Figure 11B:
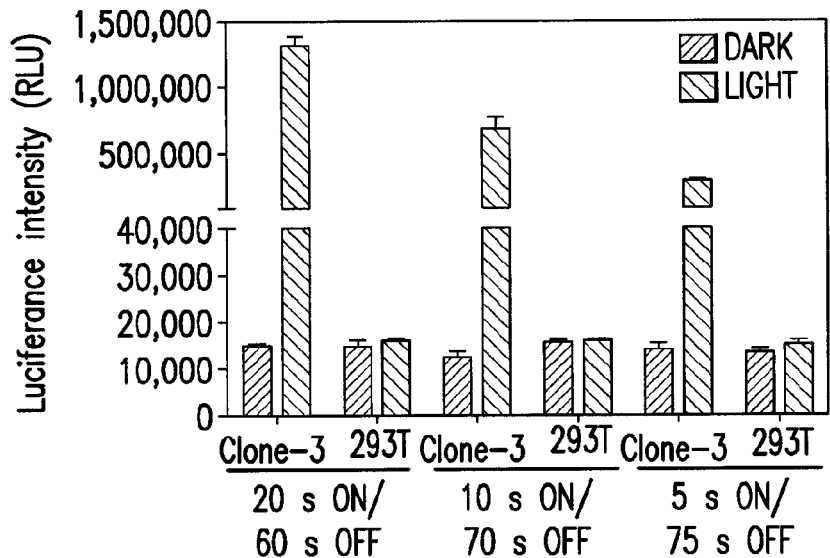
Figure 11C:
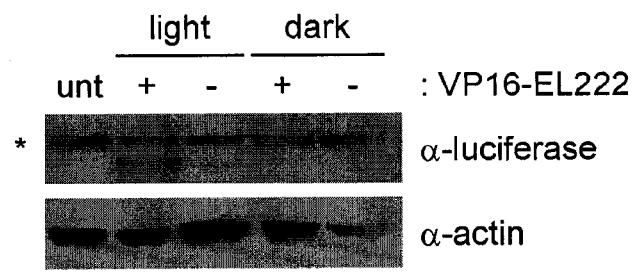

The results in FIG. 11a show that the highest level of Luciferase transcriptional activation in Clone-3 cells was achieved after 12 hr of illumination. With this information in hand the parameters of the illumination schedule were tested. Three different illumination cycles were compared: 20 seconds light/60 seconds dark; 10 seconds light/70 seconds dark; and 5 seconds light/60 seconds dark. The results (shown in FIG. 11b) demonstrate that the optimal illumination schedule consists of 20 seconds light/60 seconds dark cycle for a 12 hr period.

iv. Cell Viability Assay

The CellTiter-Blue® cell viability assay (Promega; catalog no. G8080) was used, as per manufacturer's instructions, to measure cell viability after performing a constant illumination experiment as described above in section called "i. constant illumination."

v. Imaging of HEK293T Cells

An mCherry reporter construct under the control of 5 copies of 20-bp C1-2 (SEQ ID NO:69) sequence was co-transfected with the VP16-EL222 expression construct or a VP16 (empty) vector into HEK293T cells as described above. At 24 hr after transfection, the cells were kept in the dark or illuminated with blue light in an alternative fashion for 24 hours using an illumination schedule of (20 seconds light:60 seconds dark). Next, the cells were analyzed using a Nikon Eclipse TS100 fluorescence microscope and images captured using NIS-Elements imaging software. A surface plot representation of each of the images taken was obtained using ImageJ software. The results are provided in FIG. 9. Cells expressing VP16-EL222 and that were illuminated with blue light showed high levels of mCherry fluorescence, indicative of transcriptional activation by VP16-EL222. However, cells transfected with VP16-EL222 that were kept in the dark showed little to no mCherry fluorescence.

Similar experiments were done with the Clone-3 cell line that stably expresses the VP16-EL222 protein. In this case, Clone-3 cells were transfected with the pClone 1-20 [mCherry] vector only and subsequently illuminated with blue light pulses (20 seconds light/60 seconds dark) for 24 hr. Cells were then analyzed using a Nikon Eclipse TS100 fluorescence microscope as described above. The number of mCherry positive cells was higher and the intensity of the fluorescent higher in Clone-3 cells than in HEK293T cells that were transiently transfected with VP16-EL222 (compare FIG. 9 and FIG. 12). These data together with the results presented in FIG. 11 suggest there is a notable advantage to using a cell line that stably expresses the VP16-EL222 protein.

vi. Western Blotting to Determine Luciferase Protein Levels in HEK293T Cells that Stably Express VP16-EL222

Clone-3 cells were plated at a density of 2.2 million cells/mL in a total volume of 2 mL in a 6-well plate. The next day cells were transfected with the Luciferase reporter vector containing 5 copies of 20-bp C1-2 (SEQ ID NO:69) sequence as described above. Immediately after transfections cells were either kept in the dark or illuminated with blue light pulses using a 10 seconds light/70 seconds dark cycle for 12 hr. Next cell lysates were made from dark and illuminated samples, approximately 10-20 µg of protein was loaded on a SDS-PAGE gel and resolved by electrophoresis. The proteins resolved from the gel were transferred to a PVDF membrane (GE Healthcare) and blotted with an anti-VP16 antibody (Abcam; ab4808). The results are provided in FIG. 11c. These data show that Luciferase protein is expressed exclusively when VP16-EL222 is present in cells and only when those cells are illuminated with blue light.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A recombinant nucleic acid molecule comprising a polynucleotide sequence encoding a light responsive DNA binding protein (LRDP) comprising:

a) a light-oxygen-voltage (LOV) domain; and
b) a DNA binding domain (DBD),
wherein said LOV domain and DBD are from *Erythrobacter litoralis* 222 amino acid protein (EL222), and wherein said sequence encoding said LRDP is operatively linked to a polynucleotide encoding a heterologous transcriptional activation domain.

2. The recombinant nucleic acid molecule of claim 1, wherein the recombinant nucleic acid molecule comprises the polynucleotide sequence of SEQ ID NO: 70, or wherein the recombinant nucleic acid encodes a polypeptide comprising the polypeptide sequence of SEQ ID NO: 71.

3. The recombinant nucleic acid molecule of claim 1, wherein the recombinant nucleic acid molecule encodes a polypeptide selected from the group consisting of SEQ ID NO: 73-85.

4. A cell in culture comprising the nucleic acid molecule of claim 1.

5. The cell in culture of claim 4 further comprising a recombinant nucleic acid molecule comprising a DNA binding site recognized by an EL222 DBD sequence operably linked to a heterologous transcribable polynucleotide sequence, wherein said DNA binding site comprises a sequence selected from the group consisting of SEQ ID NO: 4, 64, 68, and 69.

6. The cell in culture of claim 4, wherein said cell is selected from the group consisting of bacterial cell, yeast cell, mammalian cell, insect cell, and plant cell.

7. A cell in culture comprising the nucleic acid molecule of claim 1 and a second nucleic acid molecule comprising a DNA binding site recognized by the EL222 DBD operably linked to a heterologous transcribable polynucleotide sequence, wherein said DNA binding site comprises a sequence selected from the group consisting of SEQ ID NO: 4, 64, 68, and 69.

8. A polypeptide encoded by the nucleic acid molecule of claim 1.

9. A cell in culture comprising the polypeptide of claim 8.

10. A recombinant nucleic acid molecule comprising a DNA binding site recognized by an EL222 DBD operably linked to a heterologous transcribable polynucleotide sequence, wherein said DNA binding site comprises a sequence selected from the group consisting of SEQ ID NO: 4, 64, 68, and 69.

11. The nucleic acid molecule of claim 10, wherein said heterologous, transcribable polynucleotide sequence is selected from the group consisting of a reporter sequence, a cell stress tolerance sequence, an industrial enzyme encoding sequence, a sequence encoding a biofuel production enzyme, a sequence encoding a cell lysis protein, and a sequence encoding a cell regulatory protein.

12. A cell in culture comprising the nucleic acid molecule of claim 10.

13. A method of activating transcription in a cell comprising illuminating the cell of claim 7 with blue light.

14. The method of claim 13, wherein said transcription is activated by at least 10×, 20×, 50×, or 100×relative to transcription in the absence of blue light.

15. A method of inactivating blue-light induced transcription comprising diminishing blue light exposure of the cell of claim 7.

* * * * *